(12) United States Patent
Adkisson

(10) Patent No.: US 6,645,764 B1
(45) Date of Patent: Nov. 11, 2003

(54) NEOCARTILAGE AND METHODS OF USE

(75) Inventor: Huston D. Adkisson, St. Louis, MO (US)

(73) Assignee: Barnes-Jewish Hospital, St. Louis, MO (US)

( * ) Notice: Subject to any disclaimer, the term of this patent is extended or adjusted under 35 U.S.C. 154(b) by 0 days.

(21) Appl. No.: 09/467,520

(22) Filed: Dec. 21, 1999

Related U.S. Application Data

(62) Division of application No. 09/054,913, filed on Apr. 3, 1998, now Pat. No. 6,235,316.
(60) Provisional application No. 60/043,369, filed on Apr. 4, 1997.

(51) Int. Cl.[7] ............................................. C12N 5/00
(52) U.S. Cl. ..................... 435/375; 435/377; 435/395
(58) Field of Search ................................. 435/375, 377, 435/395

(56) References Cited

U.S. PATENT DOCUMENTS

| | | | |
|---|---|---|---|
| 4,642,120 A | 2/1987 | Nevo et al. ................... 623/16 |
| 4,846,835 A | 7/1989 | Grande ......................... 623/11 |
| 4,877,864 A | 10/1989 | Wang et al. ................. 435/324 |
| 5,041,138 A | 8/1991 | Vacanti et al. ................ 623/16 |
| 5,326,357 A | 7/1994 | Kandel ......................... 623/16 |
| 5,368,051 A | 11/1994 | Dunn et al. .................. 128/898 |
| 5,585,237 A | 12/1996 | Oppermann et al. ........... 435/6 |
| 5,658,882 A | 8/1997 | Celeste et al. ................ 514/12 |
| 5,688,678 A | 11/1997 | Hewick et al. .......... 435/240.2 |
| 5,709,854 A | 1/1998 | Griffith-Cima et al. .... 424/93.7 |
| 5,723,331 A | 3/1998 | Tubo et al. .................. 435/366 |
| 5,736,372 A | 4/1998 | Vacanti et al. .............. 435/180 |
| 5,770,193 A | 6/1998 | Vacanti et al. ............. 424/93.7 |
| 5,786,217 A | 7/1998 | Tubo et al. .................. 435/402 |
| 5,902,741 A | 5/1999 | Purchio et al. ............. 435/325 |

FOREIGN PATENT DOCUMENTS

| | | |
|---|---|---|
| EP | 0 739 631 | 10/1996 |
| WO | WO 94/09118 A1 | 10/1993 |
| WO | WO 98/04681 A2 | 7/1997 |

OTHER PUBLICATIONS

Adkisson et al, FASEB Journal, vol. 5, pp. 344–353, Mar. (1991).
Fedewa et al.; "Chondrocytes in Culture Produce a Mechanically Functional Tissue"; J. Orthopaedic Research 16:227–236 (1998).
Osman et al.; "Combined Transgenic Expression of α–galactosidase and α1 2–Fucosyltransferase Leads to Optimal Reduction in the Major Xenoepitope Galα(1, 3)Gal", Proc. Natl. Acad. Sci. USA 94:14677–14682 (1997).
Jürgensen et al.; "A New Biological Glue for Cartilage–Cartilage Interfaces: Tissue Transglutaminase"; J. Bone and Joint Surg. 79A:185–193 (1997).
Roughley et al.; Biochem. J., Vo. 295, pp. 421–426 (1993).
Sandrin et al.; "Reduction of the Major Porcine Xenoantigen Galα(1,3)Gal by Expression of α(1,2)fucosyltransferase"; Xenotransplantation 3:134–140 (1996).
Sandrin et al.; "Enzyme Remodeling of the Carbohydrate Surface of a Xenogenic Cell Substantially Reduces Human Antibody Binding and Complement–mediated Cytolysis"; Nature Med. 1:1261–1267 (1995).
Brittberg et al.; "Treatment of Deep Cartilage Defects in the Knee with Autologous Chondrocyte Transplantation"; N. Eng. J. Med. 331:889–895 (1994).
Cleland et al.; "Inhibition of Human Neutrophil Leukotriene $B_4$ Synthesis in Essential Fatty Acid Deficiency: Role of Leukotriene A Hydrolase"; Lipids 29:151–155 (1994).
Reginato et al.; "Formation of Nodular Structures Resembling Mature Articular Cartilage in Long–Term Primary Cultures of Human Fetal Epiphyseal Chondrocytes on a Hydrogel Substrate"; Arthritis & Rheumatism 37:1338–1349 (1994).
Lee et al.; "Conversion to an Elastogenic Phenotype by Fetal Hyaline Chondrocytes is Accompanied by Altered Expression of Elastin–Related Macromolecules"; Dev. Biol. 163:241–252 (1994).
Jobanputra et al.; "Cellular Responses to Human Chondrocytes: Absence of Allogenic Responses in the Presence of HLA–DR and ICAM–1"; Clin. Exp. Immunol. 90:336–344 (1992).
Schreiner et al.; "Essential Fatty Acid Depletion of Renal Allografts and Prevention of Rejection"; Science 240:1032–1033 (1988).
Jahn et al.; "Changes in Cell Surface Antigen Expression on Human Articular Chondrocytes Induced by Gamma–Interferon"; Arthritis & Rheumatism 30:64–74 (1987).
Gertzbein et al.; "The Stimulation of Lymphocytes by Chondrocytes in Mixed Cultures"; Clin. Exp. Immunol. 24:102–109 (1976).
Elves M.W.; "A Study of the Transplantation Antigens on Chondrocytes from Articular Cartilage"; J. Bone Joint Surg. 56B:178–185 (1974).

(List continued on next page.)

Primary Examiner—Jean C. Witz
(74) Attorney, Agent, or Firm—Sonnenschein Nath & Rosenthal

(57) ABSTRACT

Disclosed are neocartilage compositions characterized by having multiple layers of cells, said cells being surrounded by a substantially continuous insoluble glycosaminoglycan and collagen-enriched hyaline extra-cellular matrix, and which neocartilage phospholipids are advantageously enriched in anti-inflammatory n-9 fatty acids, particularly 20:3 n-9 eicosatrienoic or Mead acid.

Also disclosed are methods of growing neocartilage in substantially serum-free growth media and methods of producing a conditioned growth media containing compounds effective to enhance neocartilage formation.

The neocartilage compositions are useful as implants and as replacement tissue for damaged or defective cartilage and as a model system for studying articular cartilage disease and response to natural and synthetic compounds.

28 Claims, 25 Drawing Sheets

OTHER PUBLICATIONS

Hale, Laura V. et al.; "Development Of A New Serum–Free Medium, USC–HC1, For Growth And Normal Phenotype In Postembryonic Chicken Growth Plate Chondrocytes"; In Vitro Cellular & Developmental Biology; vol. 22, No. 10; pp. 597–603; 1986.

Jennings, Susan D. et al.; "Clonal Growth of Primary Cultures of Rabbit Ear Chondrocytes In a Lipid–Supplemented Defined Medium"; Experimental Cel Research 145; pp. 415–423; 1983.

Tamponnet, Christian et al.; "Rabbit Articular Chondrocytes In Alginate Gel: Characterisation Of Immobilized Preparations And Potential Applications"; Appl. Microbiol Biotechnol 37; pp. 311–315; 1992.

FIG. 5A  FIG. 5B
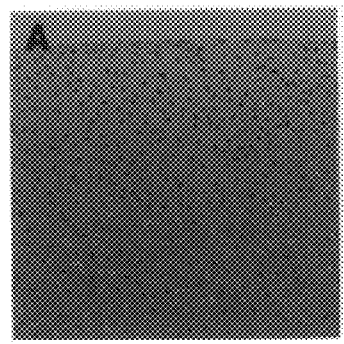 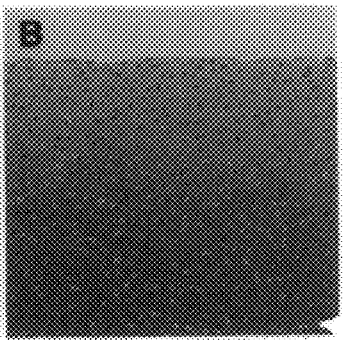
FIG. 5C  FIG. 5D
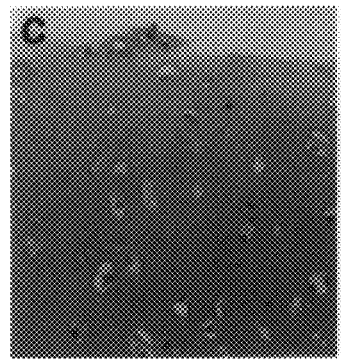 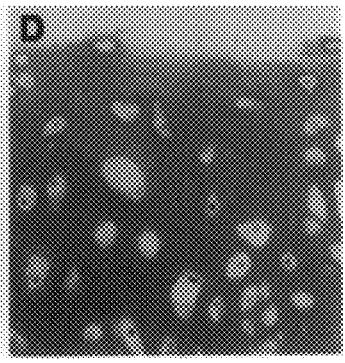
FIG. 5E  FIG. 5F
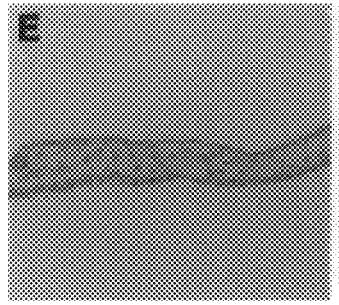 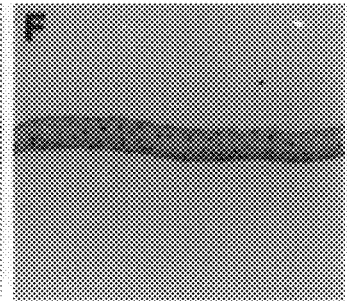

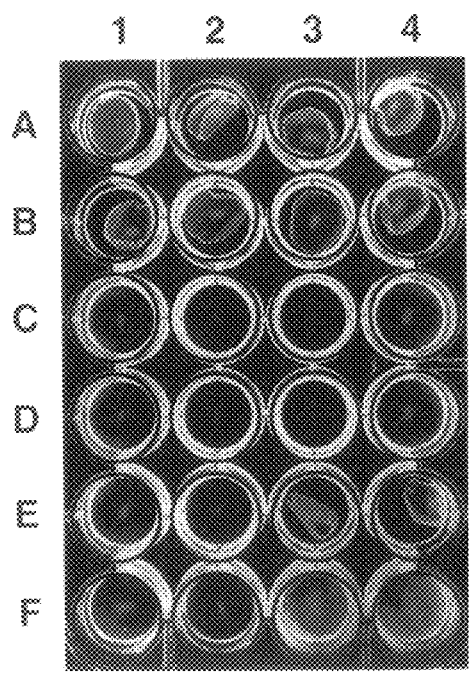 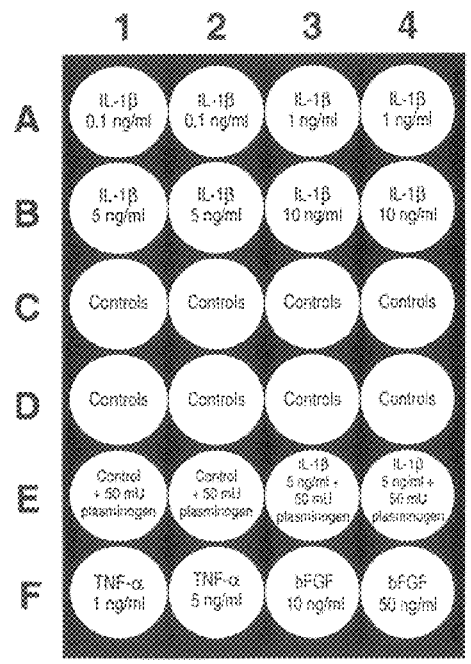

FIG. IIA
A
FIG. IIB
B
1 2 3 4 5 6

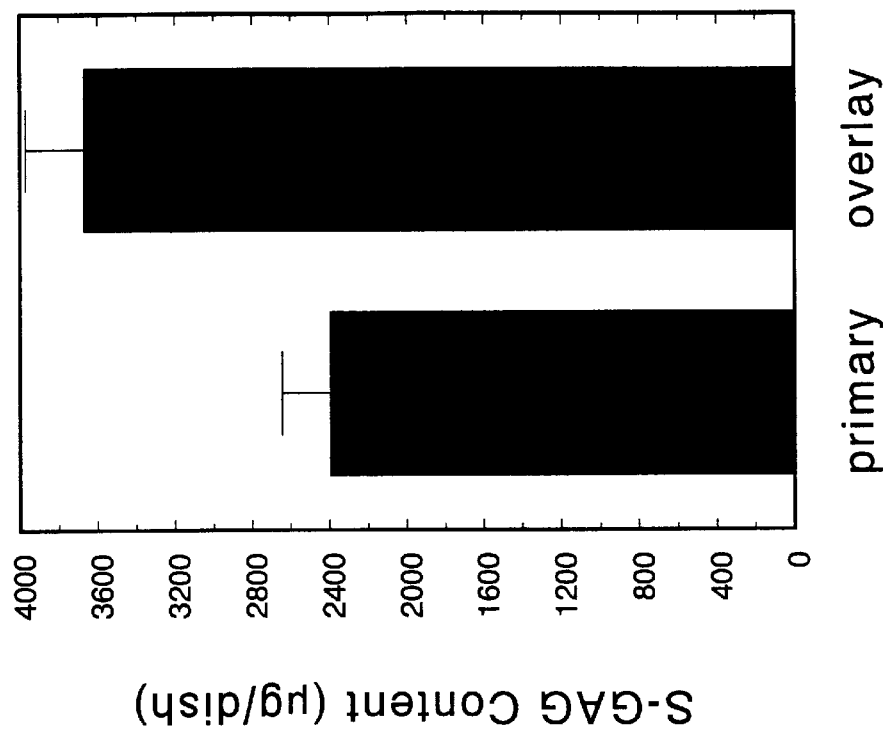
FIG. 16 Chondrocyte Overlay Increases Neocartilage S-GAG Content
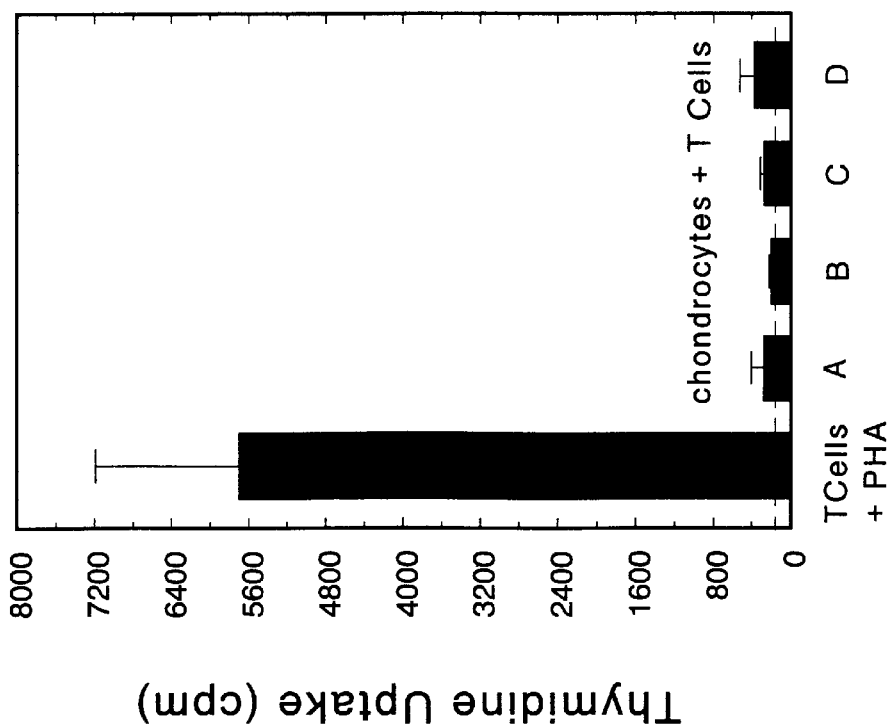
FIG. 15 Chondrocyte Costimulatory Function FATTY ACID COMPOSITION OF HUMAN FETAL ARTICULAR CHONDROCYTE PHOSPHOLIPIDS
Linoleate FATTY ACID COMPOSITION OF HUMAN FETAL ARTICULAR CHONDROCYTE PHOSPHOLIPIDS
Dihomo-γ-linolenate FATTY ACID COMPOSITION OF HUMAN FETAL ARTICULAR CHONDROCYTE PHOSPHOLIPIDS
Arachidonate FATTY ACID COMPOSITION OF HUMAN FETAL ARTICULAR CHONDROCYTE PHOSPHOLIPIDS
16:1 n-9 + n-7

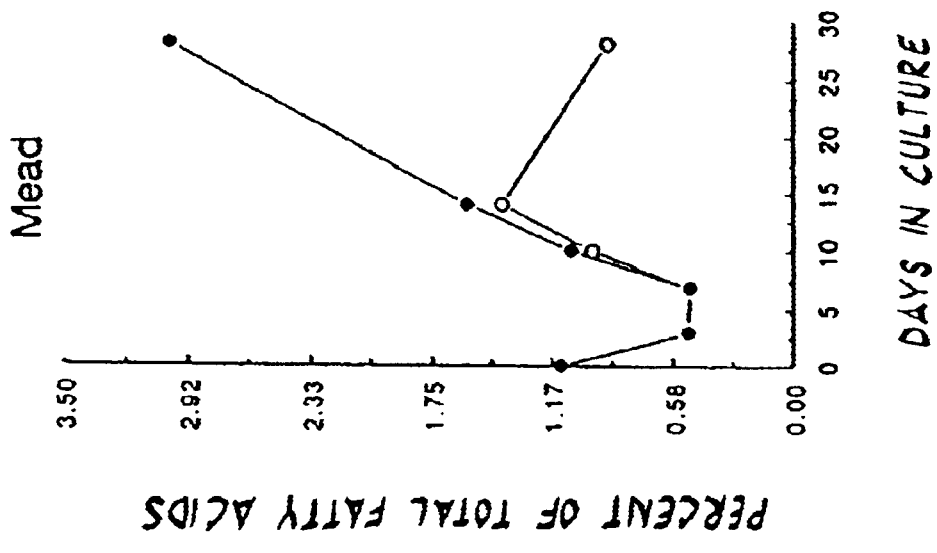
FIG. 20F FATTY ACID COMPOSITION OF HUMAN FETAL ARTICULAR CHONDROCYTE PHOSPHOLIPIDS
Mead
FIG. 20E FATTY ACID COMPOSITION OF HUMAN FETAL ARTICULAR CHONDROCYTE PHOSPHOLIPIDS
18:1 n-9 + n-7

NEOCARTILAGE AND METHODS OF USE

This application is a divisional application of application Ser. No. 09/054913, filed Apr. 3, 1998, which issued as U.S. Pat. No. 6,235,316 B1 on May 22, 2001, which claims priority from U.S. Provisional Application Serial No. 60/043369, filed Apr. 4, 1997, which is incorporated herein by reference.

BACKGROUND OF THE INVENTION

This invention relates generally to novel neocartilage compositions useful as implants and as replacement tissue for damaged or defective cartilage, as model systems for studying articular cartilage disease and articular cartilage response to natural and synthetic compounds and for the isolation of cartilage derived substances useful in the biotechnology industry.

More specifically, the invention concerns neocartilage, particularly human neocartilage, having multiple layers of cells surrounded by a substantially continuous insoluble glycosaminoglycan and collagen-enriched hyaline extracellular matrix, and whose membrane phospholipids are enriched in the anti-inflammatory n-9 fatty acids, particularly 20:3 n-9 eicosatrienoic or Mead acid. Also provided are methods of producing neocartilage in vitro by growing chondrocytes in substantially serum-free growth media. The invention further relates to methods for producing conditioned growth media comprising compounds effective to enhance neocartilage formation, and for the isolation of cartilage derived substances.

Unlike most tissues, adult articular cartilage does not self-repair. Normal articular cartilage is hyaline cartilage comprising a distinctive combination of cartilage-specific collagens (types II, VI, IX, and XI) and aggregating proteoglycans (aggrecan) which give it the unique ability to withstand compressive forces.

Chondrocytes are the cartilage-specific cells which give rise to normal articular cartilage tissue growth in vivo. Adult chondrocytes, however, have generally lost their potential to reproduce and generate new cartilage in vivo, although they are responsible for maintaining tissue homeostasis.

Attempts to grow human articular cartilage using traditional cell culture methods such as growing chondrocytes on tissue-culture plastic surfaces using serum-containing growth media have proved unsuccessful. Although serum (the non-red blood cell portion of blood, clotted and spun down) is known to be a potent mitogen to chondrocytes, their culture in serum-containing growth media has been reported to result in dedifferentiation of the chondrocyte phenotype.

It is also well known in the art that growing chondrocytes in monolayers on plastic culture vessels for prolonged periods leads to loss of their spherical shape and the acquisition of an elongated fibroblastic morphology. Reginato, et al., *Arthritis & Rheumatism* 37: 1338–1359 (1994). Biochemical changes associated with this morphological change include loss of the articular cartilage phenotype, e.g., loss of rounded cell shape, an arrest of cartilage-specific collagen and proteoglycan synthesis, the initiation of collagen type I and III synthesis, and an increase in small non-aggregating proteoglycan synthesis. Reginato, et al., supra.

Adult human chondrocytes grown directly on tissue-culture plastic in growth media containing serum, attach to the plastic substrate and fail to deposit an insoluble matrix enriched in glycosaminoglycan. Glycosaminoglycan is the proteoglycan component essential to the physiological function of articular cartilage and is the hallmark of hyaline tissue. The extracellular matrix initially produced by methods using serum-containing growth media is not enriched in glycosaminoglycan and resorption of the matrix material occurs as the cell culture ages.

Attempts to overcome chondrocyte dedifferentiation in vitro have included culturing chondrocytes at high densities and growing them in suspension culture or on substrata that prevent cellular spreading and attachment to the tissue-culture plastic. Reginato et al. described a method of growing human fetal chondrocytes cultured on polyHEMA-coated plastic dishes in a serum-supplemented DMEM growth media. *Arthritis & Rheumatism* 37: 1338–1359 (1994). This method was successful at maintaining the cartilage-specific phenotype but produced only nodules resembling articular cartilage, not a continuous layer of articular cartilage tissue.

Kuettner described in U.S. Pat. No. 4,356,262, a method of producing bovine cartilaginous tissue from which an anti-invasion factor may be recovered. This method provided culturing a monolayer of chondrocytes at high densities in a suspension of serum-containing growth media in a roller bottle. This method produced nodules of tissue having an extracellular matrix, but not a continuous layer of articular cartilage tissue.

Another method that prevents chondrocyte attachment to tissue culture plastic is described in Kandel, U.S. Pat. No. 5,326,357. Kandel described methods of reconstituting bovine cartilage tissue in vitro by seeding chondrocytes on a porous tissue culture insert substrate which had been coated with type I collagen to facilitate chondrocyte attachment and growth in a serum-containing growth media. The tissue culture insert is used to separate the chondrocytes from the tissue culture plastic. This method produced a continuous cartilaginous tissue having zones of elongated and spherical chondrocytes which resemble native bovine cartilage.

Without a readily available replacement tissue, recent methods of articular cartilage repair have focused on biological resurfacing of cartilage defects with either a prosthetic device or with live chondrocytes. Methods of in vivo articular cartilage repair include transplanting chondrocytes as injectable cells or as a composition of cells embedded in a three-dimensional scaffold. These methods, like in vitro neocartilage production, have been less than completely successful. One such repair method is autogenous chondrocyte transplantation. Vacanti et al., WO 90/12603. In this method, normal chondrocytes obtained from the patient are surgically removed, cultured to increase cell number and then injected into the defective site and secured in place with a periosteal flap. Brittberg, M., et al., *N. Eng. J. of Med.*, 331:889–895 (1994). This method requires two separate surgical procedures to complete.

Allograft transplant methods, which require a single surgery, use implants made of donor chondrocytes seeded and grown on a natural or synthetic three dimensional scaffold (Vacanti, et al., U.S. Pat. No. 5,041,138; Gendler, EP 0739631 A2). In these methods, the natural or synthetic three-dimensional scaffold is provided to give the cell culture structure and to mimic the natural extracellular matrix while the cartilage tissue is produced in vivo.

It has recently been shown, however, that neither the autogenous nor the allogenic transplant method results in consistent growth of articular cartilage in vivo, but rather results in chondrocyte dedifferentiation and formation of fibrocartilage. Because of the reduced aggrecan content of fibrocartilage, it cannot withstand the same biomechanical stresses as articular cartilage. Fibrocartilage degenerates with use, and its formation following joint repair may promote joint dysfunction and permanent disability.

In addition to the clinical need for readily available replacement tissue, healthy articular cartilage is needed for use in model systems for studying articular cartilage disease and to evaluate chondrocyte responses to growth factors, cytokines and pharmaceutical compositions.

Osteoarthritis, the most common form of arthritic disease, affects almost 16 million people in the United States alone. Osteoarthritis is characterized by the appearance of focal lesions at the cartilage surface. With advancing age and disease progression, these changes are accompanied by a marked reduction in proteoglycan content, extensive destruction of the collagen framework, a marked increase in tissue hydration, and subsequent joint dysfunction.

Osteoarthritis appears to develop within the articular cartilage of weight-bearing joints, particularly joints of the knee, hip, hand, and foot. Under normal physiological conditions, cartilage homeostasis is maintained by the resident chondrocytes. This highly specialized cell functions to synthesize, assemble, and remodel all components of cartilage extracellular matrix, including aggregating proteoglycan as well as collagens type II, VI, IX, and XI. Despite intensive research efforts to ascertain the biological basis of osteoarthritis, its development and progression remain poorly understood.

Recent studies attempting to characterize collagenolytic activity in human osteoarthritis indicate a clear need for a reliable alternative to animal models for elucidating early biological events of disease progression. Most animal tissues do not express the complexity of enzymes that have been implicated in human disease. Thus, animal models are inadequate for evaluating the efficacy of potential disease modifying agents in human osteoarthritis.

A shortage of normal articular cartilage for studying articular cartilage disease and articular cartilage response to natural and synthetic compounds exists because the only source of healthy articular cartilage currently available is from deceased adult donors which may show degenerative changes.

BRIEF SUMMARY OF THE INVENTION

Among the several objects of the invention, therefore, may be noted:

the provision of novel neocartilage compositions and uses thereof;

the provision of methods of producing such novel neocartilage compositions and methods of producing conditioned growth media for use therein, and the provision of cartilage specific components useful in tissue engineering.

The neocartilage of the invention is useful, for example, as replacement tissue for damaged or defective cartilage and as a model system for studying articular cartilage disease and response to natural and synthetic compounds. Illustratively, surgical implants, or allografts, of the neocartilage were created in vitro and surgically attached to natural cartilage in animal models to repair surgically created defects.

Briefly, therefore, the present invention is directed to neocartilage characterized by one or more of the following attributes: containing membrane phospholipids enriched in Mead acid, containing membrane phospholipids depleted in linoleic or arachidonic acid, being substantially free of endothelial, bone and/or synovial cells, having a S-GAG content of at least about 400 mg/mg of OH-proline, being substantially free of type I, III and X collagen, containing a matrix substantially free of biglycan, being enriched in high molecular weight aggrecan, being produced in vitro using serum-free growth medium, being essentially free of non-cartilage material, and being characterized by having multiple layers of cells surrounded by a substantially continuous insoluble glycosaminoglycan and collagen-enriched hyaline extracellular matrix.

The present invention is further directed to methods of growing neocartilage in substantially serum-free growth media. Initially, chondrocytes are isolated and adhered to a surface using means effective to produce a monolayer cell culture. The cell culture is then grown in a substantially serum-free cell culture to produce the neocartilage of the invention and the neocartilage so produced.

The invention is also directed to a biological material containing essentially purified cartilage-specific macromolecules.

Also provided is a conditioned growth medium adapted for use in growing cartilage cell cultures which contain heparin-binding growth factors, at least one of which is a cartilage-derived morphogenetic protein (Chang et al., *J. Biol Chem* 269:28227–28234).

In a further aspect of the invention, a set of implant materials are provided. These materials include a reparative amount of Mead acid enriched neocartilage or neocartilage produced as described above. Also included are means for implanting and adhering the neocartilage in a target tissue locus.

In yet other aspects of the invention, methods of producing a conditioned growth media comprising compounds effective to enhance neocartilage formation and such conditioned growth media are provided, and methods of producing cartilage derived compounds and such cartilage-derived compounds, using serum-free growth media, are also provided.

In an additional aspect of the invention, a method of screening a pharmaceutical for its capacity to modulate arthritic disease is provided. In this method, the neocartilage as described herein is co-cultured with the pharmaceutical in an amount and under conditions effective for determining whether characteristic indications of arthritic modulation are observed in the neocartilage.

Other objects and features will be in part apparent and in part pointed out hereinafter.

BRIEF DESCRIPTION OF THE DRAWINGS

FIG. 1, in two parts, FIGS. 1A and 1B, respectively, represent lateral and birds-eye views of human neocartilage at day 90 of culture. The structural characteristics of this hyaline cartilage mimics that of native articular cartilage.

FIG. 3, in two parts.

FIG. 4, in two parts, FIG. 4A, day 56 control neocartilage (serum-free). Notice the marked decrease in metachromatic staining which occurred in response to repletion with 10% FBS (FIG. 4B). Also notice the flattened and elongated phenotype of chondrocytes present at the surface of the neocartilage. These changes suggest that in the absence of mechanical stimulation, serum promotes autolytic resorption of hyaline cartilage matrix, the mechanism of which requires further study.

FIG. 5, in six parts, FIGS. 5A–5F shows the morphologic appearance of native and neocartilage matrix following formalin fixation and paraffin embedding. Tissue sections were cut and stained with either safranin-O (FIGS. 5A, 5C and 5E) or pentachrome (FIGS. 5B, 5D, and 5F) to visualize specific extracellular matrix components.

Safranin-O stains red and identifies S-GAG, whereas pentachrome stains yellow for collagen, green for proteoglycan, and black for elastin. Because the tissues are enriched in collagen and proteoglycan, an aqua blue color is achieved upon pentachrome staining.

FIGS. 5A and 5B show longitudinal sections of fetal proximal tibia used to create the neocartilage grafts in FIGS. 5C–5F.

FIGS. 5C and 5D represent neocartilage grown under serum-free conditions and harvested at day 90.

FIGS. 5E and 5F demonstrate the inhibitory effect of serum on neocartilage formation (day 0–30). (10% FBS). Serum supplementation caused the cell layers to ball up and slough away from the tissue culture surface after day 30. Note that FIGS. 5C and 5D show only a small fraction of the full thickness of day 90 neocartilage. Chondrocytes are seen localized to individual lacunae, forming hyaline tissue that is virtually indistinguishable in appearance from the native starting material and which spans 15–20 cell layers deep. Magnification×200 for FIGS. 5A, 5B, 5E and 5F, and ×400 for FIGS. 5C and 5D.

FIG. 6, in six parts, FIGS. 6A–6F shows the ultrastructural characterization of neocartilage matrix by transmission electron microscopy (TEM). Representative cultures from FIG. 5 were fixed with glutaraldehyde, post fixed with osmium-tetroxide, and stained en-bloc with tannic acid and uranyl acetate. Ultra-thin sections were counter-stained routinely with uranyl acetate and lead citrate. High power magnification×61,900 (B,D,F) of the ECM of native (FIGS. 6A and 6B) and neocartilage tissue grown in either the presence (FIGS. 6E and 6F), or absence (FIGS. 6C and 6D) of 10% FBS.

Figure 6A:
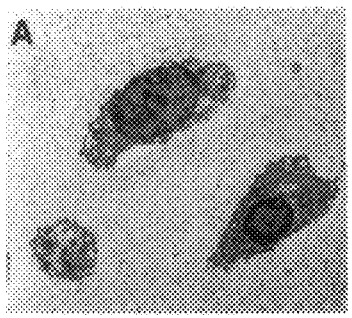
Figure 6B:
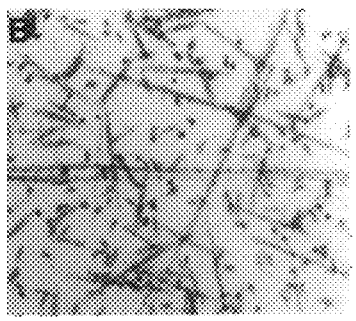
Figure 6C:
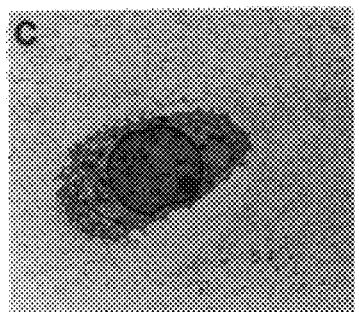
Figure 6D:
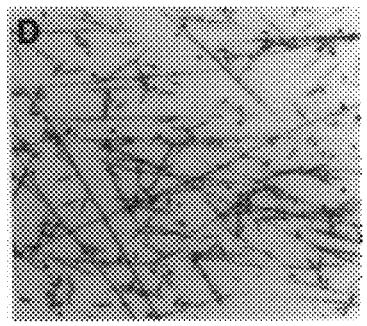
Figure 6E:
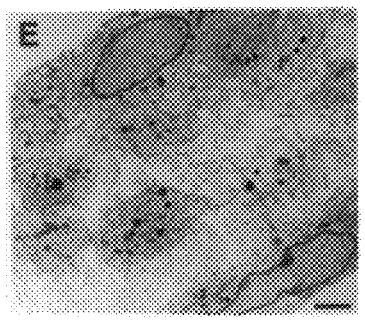
Figure 6F:
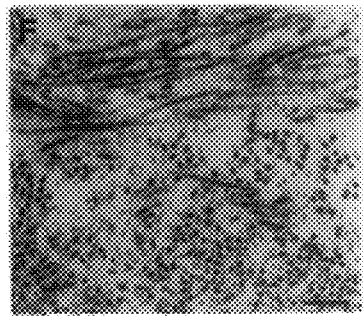

Note that FIG. 6E represents the entire thickness of the culture material and that these chondrocytes display cell/cell contact. Type II collagen (20 nm diameter fibrils) comprised the dominant structural protein in each of these tissues, confirming that the engineered tissue is hyaline in nature. Low power magnification×3,365 (A,C,E). A lack of matrix proteoglycan probably contributes to stacking of the collagen fibrils observed in FIG. 6F.

Figure 7:
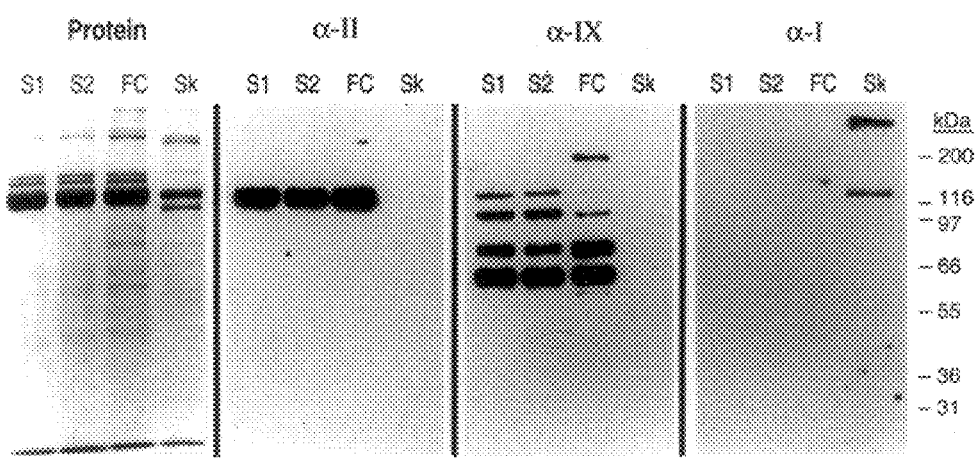

FIG. 7 shows SDS-PAGE and Western analysis of matrix associated collagen obtained by limited pepsinization and neutral salt precipitation.

S1 and S2 are duplicate samples of neocartilage tissue (day 90), while FC and Sk represent native fetal cartilage and skin, respectively.

Antibodies to collagen types-II, IX and I were obtained from Oncogene Sciences.

The analysis shows the presence of type II collagen and the absence of type I collagen. Only the positive control (fetal skin) recognized monoclonal antibody directed to collagen type I.

FIG. 8, in two parts, FIGS. 8A and 8B, shows cytokine-induced resorption of fetal articular cartilage. It is a demonstration of the relative appearance of treated and untreated neocartilage cultures showing that neocartilage exposed to cytokine is markedly reduced in size and lifts away from the plastic surface.

Tissue was propagated as described above (day 28) and stimulated with increasing concentrations of the indicated cytokine or growth factor (FIG. 8B) for an additional 36 days.

Cytokines were added to fresh ascorbate containing media every 48 hours.

Spent media was collected and frozen at each feeding for analysis of S-GAG, hydroxyproline content, and matrix metalloproteinase (MMP) synthesis.

Likewise, remnant neocartilage was frozen for chemical analysis of ECM components.

Note that in each case, the IL-1 and TNF-treated samples retracted considerably upon removal from the plastic surface (FIG. 8A), implying that increased synthesis and activation of the MMPs reduced the structural integrity of the tissue.

FIG. 9, in four parts, FIGS. 9A–9D, shows a comparison of the extracellular matrix of control (FIGS. 9A and 9B) and activated (FIGS. 9C and 9D) neocartilage following stimulation with interleukin-1. It is seen that chronic IL-1 stimulation alters cartilage staining for proteoglycan and collagen.

Day 60 neocartilages were treated with 1 ng/ml rhIL-1β for 30 days. Fresh media and cytokine were added every 48 hours.

Figure 9A:
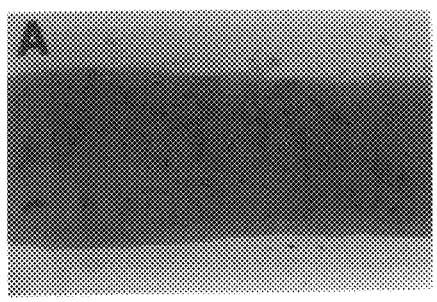
Figure 9B:
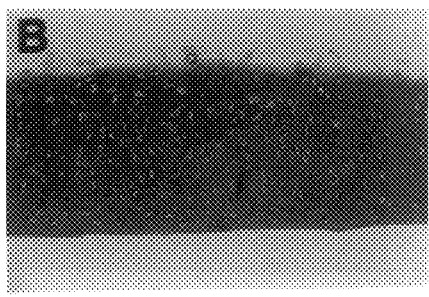
Figure 9C:
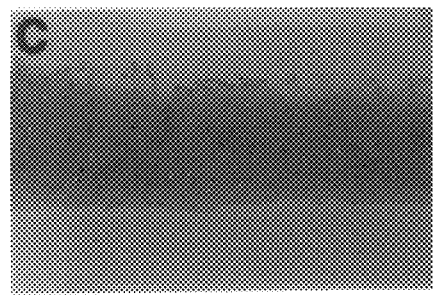
Figure 9D:
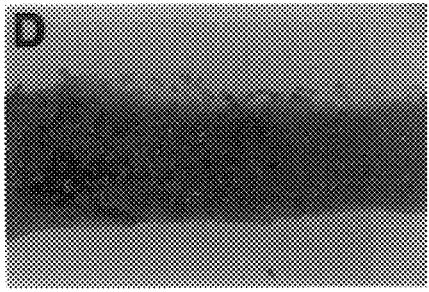

Neocartilages were harvested (day 90) and stained with safranin-O and pentachrome as before. Staining intensity is markedly reduced in stimulated (FIGS. 9C, 9D) versus untreated controls (FIGS. 9A, 9B).

Chondrocyte activation with IL-1 caused a significant reduction in the thickness of the synthesized matrix. Altered pentachrome staining following IL-1 stimulation suggests that MMP-mediated cleavage of collagen directly affects the binding characteristics of pentachrome dye to collagen. Magnification×100.

Figure 10:
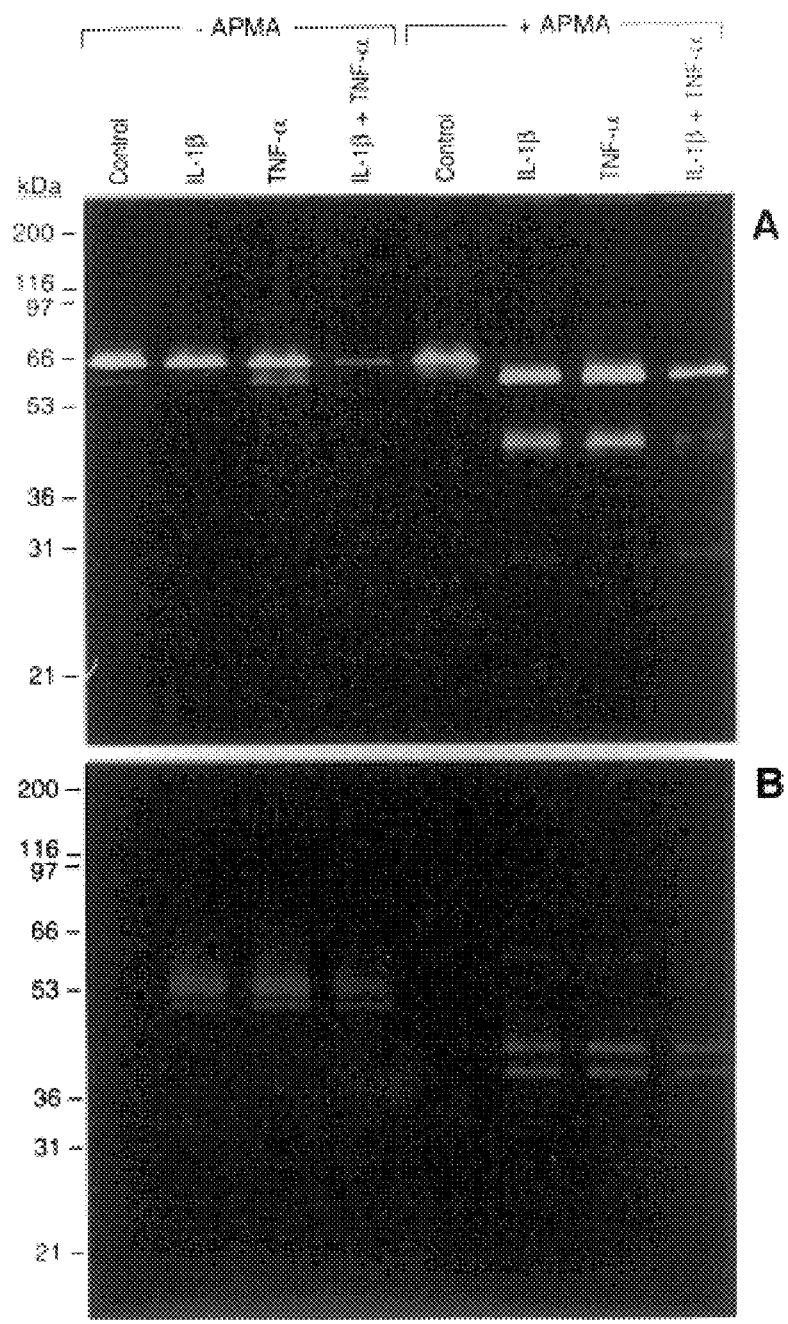

FIG. 10, in two parts, FIGS. 10A and 10B, represent SDS-substrate gel (zymogram) analysis of cytokine-mediated production of matrix metalloproteinases (MMPs) in fetal articular chondrocytes (neocartilage disks). Negative staining indicates the molecular weight (MW) in kDa of the active proteases.

- Spent media were collected 72 h post stimulation with the indicated cytokine (5 ng/ml) and concentrated 16-fold by dialysis/lyophilization.
- Unreduced samples were separated on 10% SDS substrate gels containing either gelatin (FIG. 10A) or casein (FIG. 10B) 0.1%.
- MMPs were renatured following SDS removal by extensive washing in 2.5% Triton X-100 and lytic bands visualized via negative staining with Coomassie blue, following incubation in a calcium and zinc containing buffer for 4 hr at 37° C.
- Latent enzyme activity is shown in lanes 1–4, while the corresponding active enzymes were prepared by pre-incubation with 1 mM 4-aminophenyl mercuric acetate (APMA lanes 5–8).

FIG. 11, in two parts, FIG. 11A and FIG. 11B, is an immunoblot demonstrating cytokine-induced production of collagenase-1 (FIG. 11A) and collagenase-3 (FIG. 11B) in culture media.

- Cell layers were stimulated chronically with 5 ng/ml rhIL-β and the spent media collected every 72 h.
- Twenty µl fractions were reduced and immunoblotted with monospecific polyclonal antisera to collagenase-1 (FIG. 11A) and collagenase-3 (FIG. 11B).
- Positive controls (purified recombinant protein) for each blot are shown in lane 1 and ranged in size from 50–54 kDa.
- Media control, Lane 2; unstimulated control, lanes 3–4; 3-day stimulation, lane 5; 6-day stimulation, lane 6.

Figure 12A:
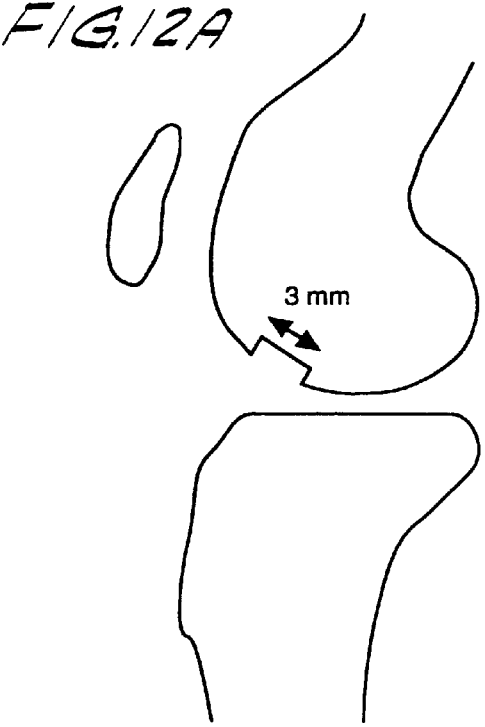
Figure 12B:
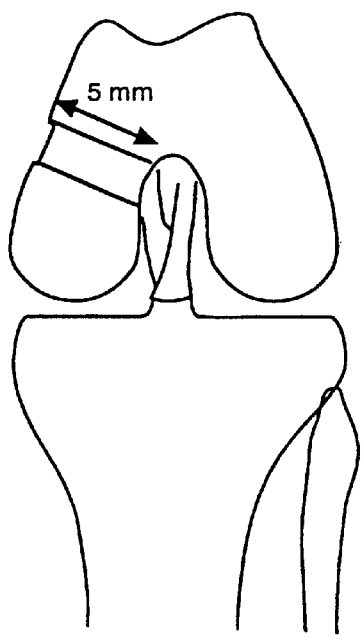
Figure 12C:
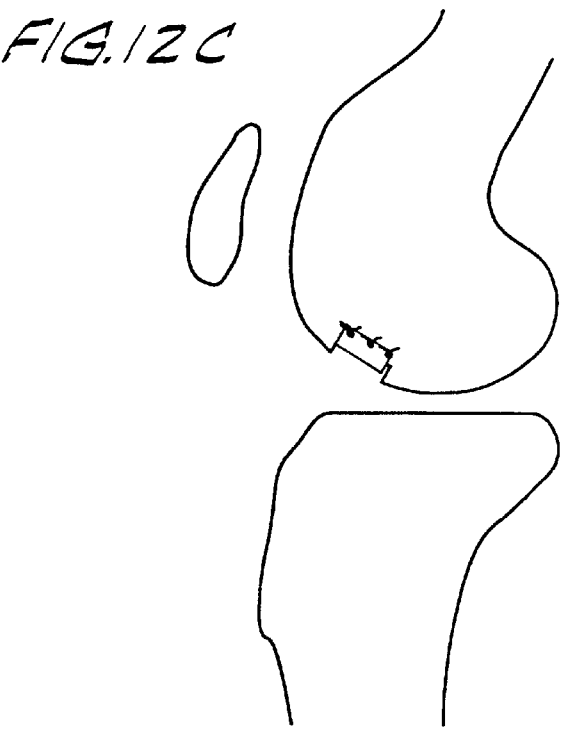
Figure 12D:
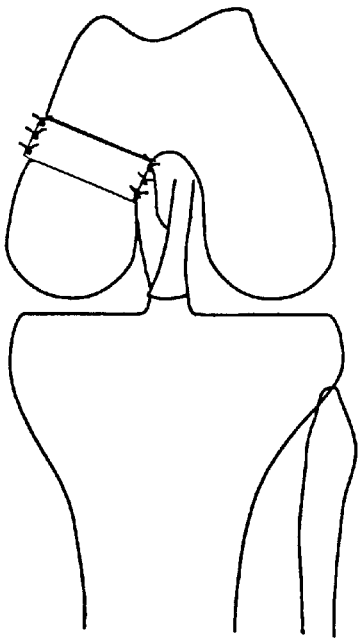

FIG. 12, in four parts, FIGS. 12A, 12B, 12C, and 12D, shows a surgical model for articular repair. Arthrotomy was performed by a medial parapatellar incision and lateral patella dislocation. A full-thickness cartilage defect, measuring 3 mm from proximal to distal traversing 5 mm from the medial edge of the medial femoral condyle, was created using a No. 15 scalpel. The defect was curetted down to, while not violating, the subchondral bony plate. The medial side of the neocartilage graft was sutured to the periosteum of the medial femur, while the lateral aspect of the graft was sutured to host cartilage at the lateral edge of the defect using 7-0 Proline sutures. After applying tissue transglutaminase (Sigma Chemical Co.) under the graft via syringe (Jurgensen et al., *J Bone Joint Surg*, 79-A:185–193, 1997), the graft-defect interface was stabilized for five minutes via finger pressure. The patella was then reduced, and the arthrotomy closed in layers with interrupted 5-0 Ethibond suture. The skin incision was closed with interrupted subcuticular 5-0 Proline sutures. Medial and anterior aspects of the operated knee are depicted in FIGS. 12A, 12C, and in FIGS. 12B, 12D, respectively.

Figure 13A:
Figure 13B:
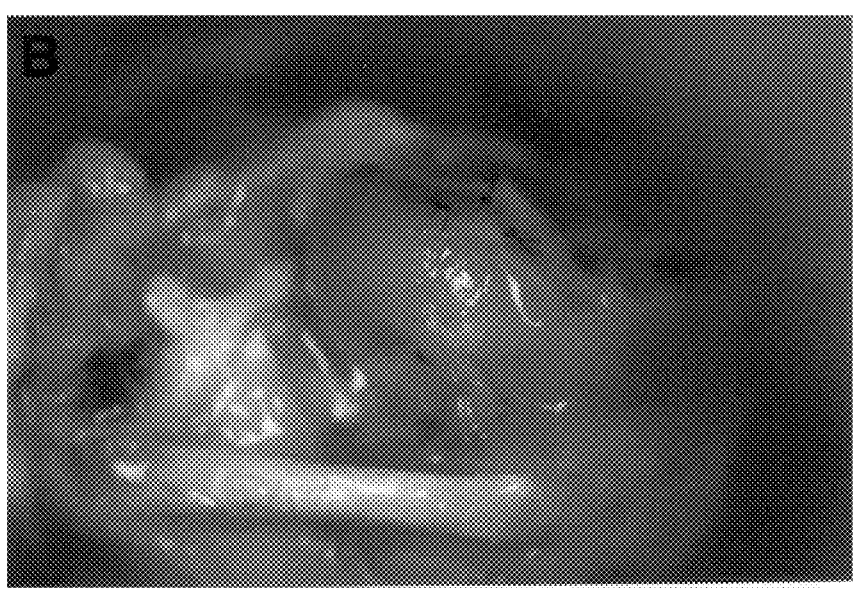

FIG. 13, in two parts, FIGS. 13A and 13B show the gross appearance of rabbit knees at harvest following surgical implantation of rabbit neocartilage. Three by 5 mm (3×5) experimental defects were created in the medial femoral condyles of 30 wk New Zealand White rabbits. Gross inspection six weeks post-operatively revealed that the neocartilage allograft was in place (FIG. 13B), and has taken on the appearance of the surrounding native cartilage. The unfilled defect of the contralateral knee remained empty (FIG. 13A).

Figure 14B:
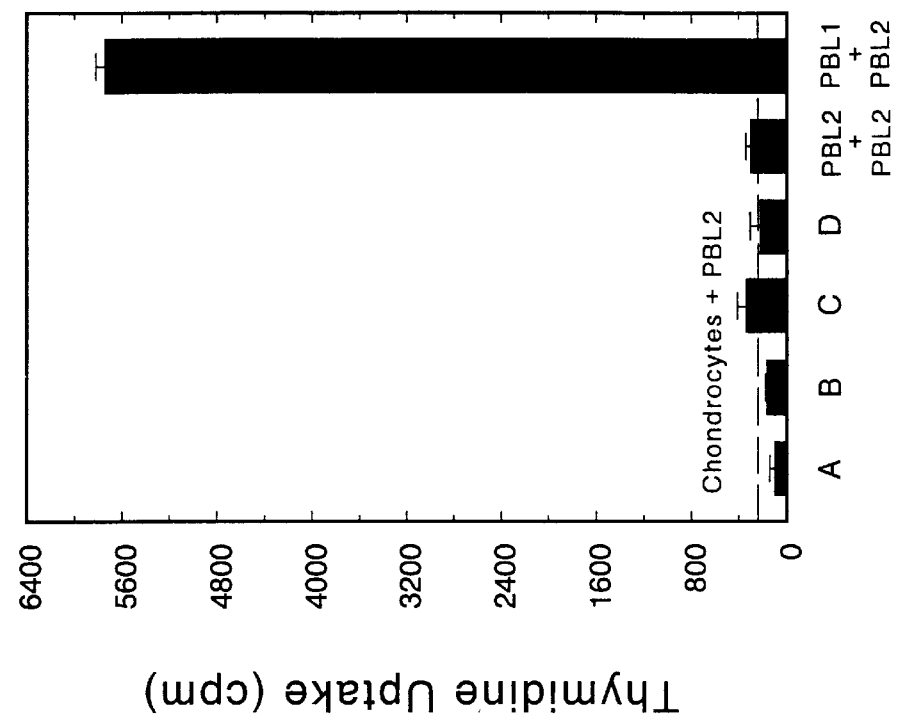
Figure 14A:
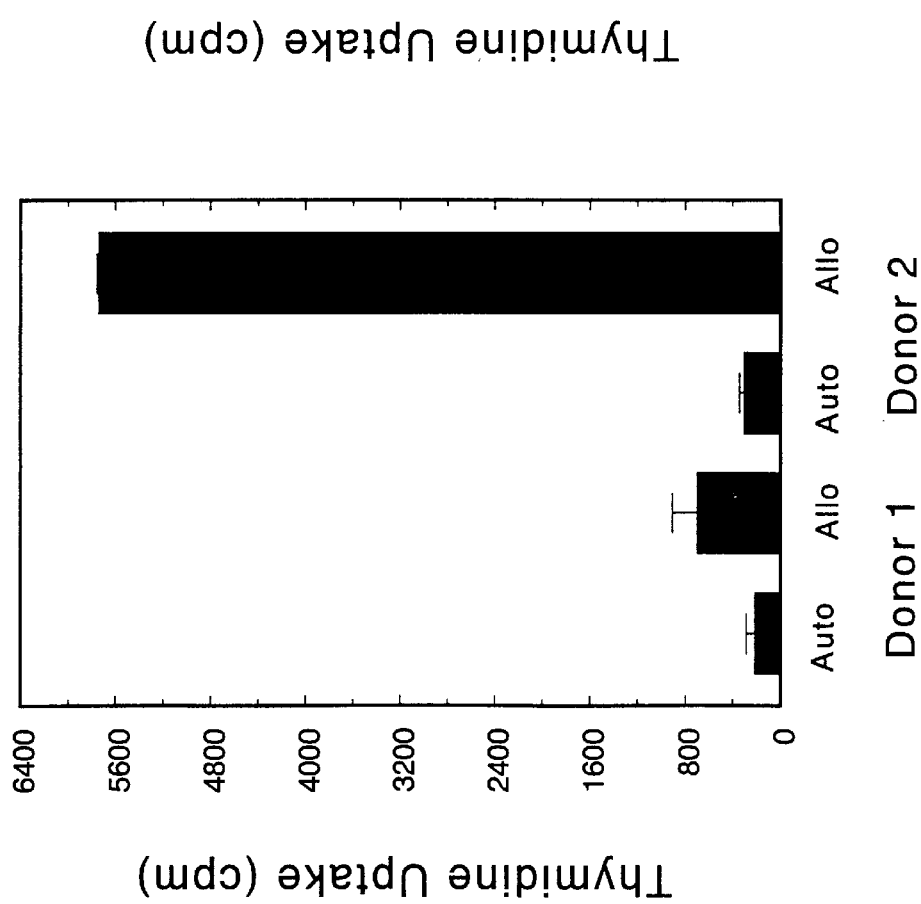

FIG. 14, in two parts, FIG. 14A and FIG. 14B, shows the results of two separate one-way mixed leukocyte assays used to measure alloreactivity via lymphocyte proliferation. The experiment in FIG. 14B was set up to investigate alloreactivity of neocartilage, following enzymatic dissociation with collagenase and hyaluronidase. Legend: A=chondrocytes isolated from day 40 neocartilage (fetal donor); B=chondrocytes isolated from day 30 culture (20 year male donor); C=chondrocytes isolated from day 30 culture (27 year male); D=chondrocytes isolated from day 30 culture (36 year female).

- In FIG. 14A, $1 \times 10^5$ irradiated peripheral blood leukocytes (PBL, American Red Cross, St. Louis, Mo.) from two unrelated donors were mixed with non-irradiated PBL from either the first (auto) or second donor (allo). Tritiated thymidine was added on day 6. Cultures were harvested and the amount of radiolabel incorporated into newly synthesized DNA counted.
- In FIG. 14B, $1 \times 10^5$ irradiated chondrocytes from four different donors of 20–36 yrs age were incubated with $1 \times 10^5$ non-irradiated PBL and their proliferation measured on day 7. Chondrocytes failed to stimulate proliferation of allogeneic PBL obtained from donor 2. Positive (allo) and negative (auto) controls were run on the same plate and are included for comparison. Legend: PBL1=peripheral blood leukocytes from unrelated donor 1; PBL2=peripheral blood leukocytes from donor 2.

FIG. 15 shows the co-stimulatory function of human neocartilage chondrocytes. $1 \times 10^5$ T-cells, semi-purified from donor 2 (FIG. 14A) using affinity columns from R & D Systems, were incubated with irradiated chondrocytes used in FIG. 14. Incubations were carried out at 37° C. for three days. Again, chondrocytes failed to stimulate a proliferative response above background.

FIG. 16 is a bar chart which shows that overlaying neocartilage with secondary passage of chondrocytes increases allograft thickness and rigidity. Day 10 human neocartilage (12 well dishes) was overlayed with $5 \times 10^5$ chondrocytes obtained via secondary passage. These cultures were harvested at day 28 and compared to control cultures that were initially seeded with $1 \times 10^6$ cells/well.

Figure 17A:
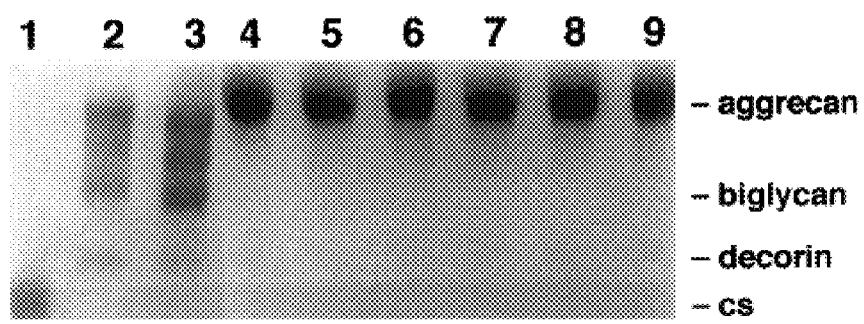
Figure 17B:
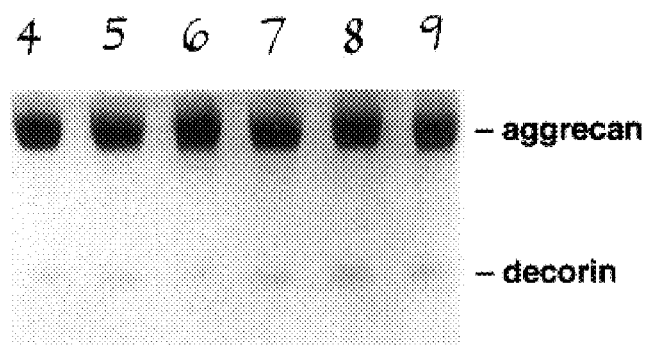

FIG. 17, in two parts, FIGS. 17A and 17B, is a characterization of neocartilage proteoglycans on 1.2% agarose gels. Human neocartilage (day 35) was labeled for 72 hr with carrier-free sodium sulfate (10 µCi/ml). Matrix proteoglycans were then guanidine extracted, ethanol precipitated, and extensively dialyzed prior to fractionation on 1.2% agarose gels. FIG. 17A, toluidine blue stained proteoglycan. FIG. 17B, autoradiograph showing localization of incorporated label in six replicates of neocartilage. Trace amounts of decorin were identified in six replicates of neocartilage, whereas biglycan, present in the 12- and 43-year subjects, was not synthesized. Lanes: 1 (chondroitin-4-sulfate standard); 2 (12-yr female); 3(43-yr male); 4–9 (replicates of human neocartilage). Note that native decorin can only be viewed in the neocartilage following metabolic labeling.

Figure 18B:
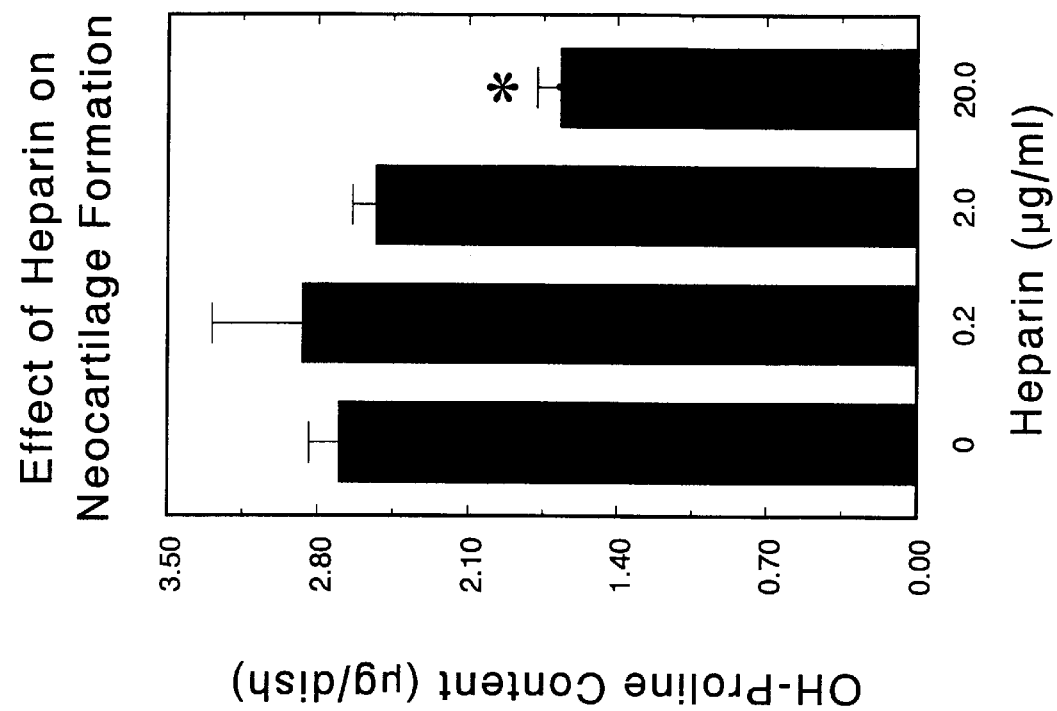
Figure 18A:
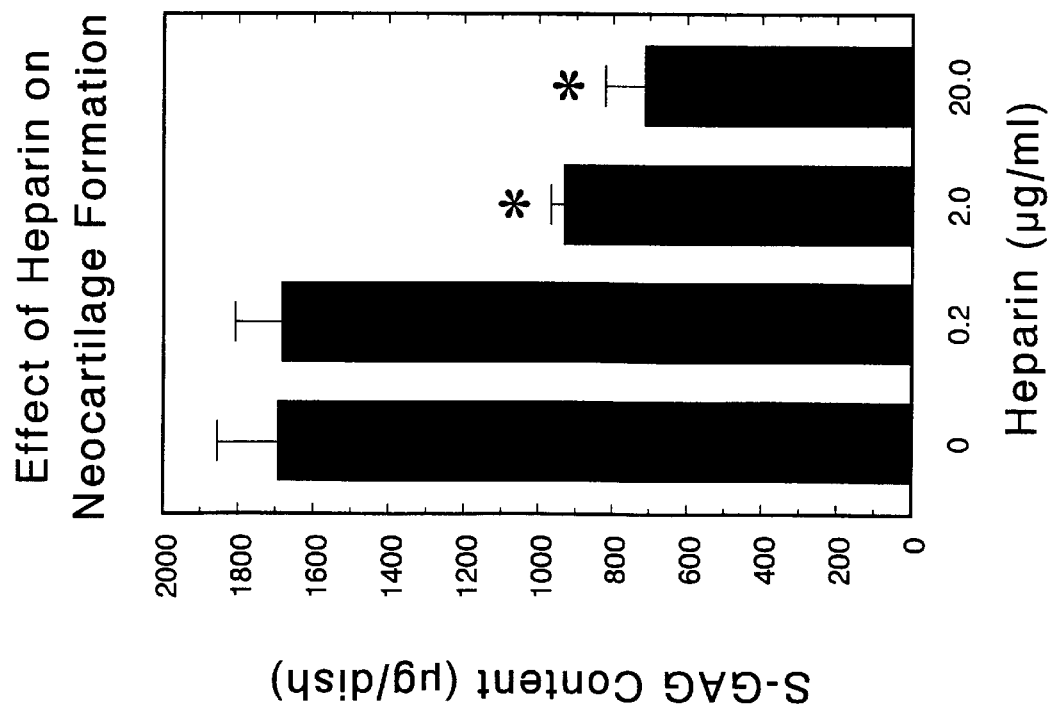

FIG. 18, in two parts, FIGS. 18A and 18B shows the effect of heparin on neocartilage formation. Day 10 neocartilage was treated with increasing amounts of heparin for 18 days. Fresh media, containing heparin and ascorbate were added every 72–96 hrs. Media were collected and frozen for future analysis. Cultures were harvested on day 28 and the S-GAG content (FIG. 18A) and OH-proline content (FIG. 18B) of the resultant neocartilage assayed as described hereinbelow.

Figure 19:
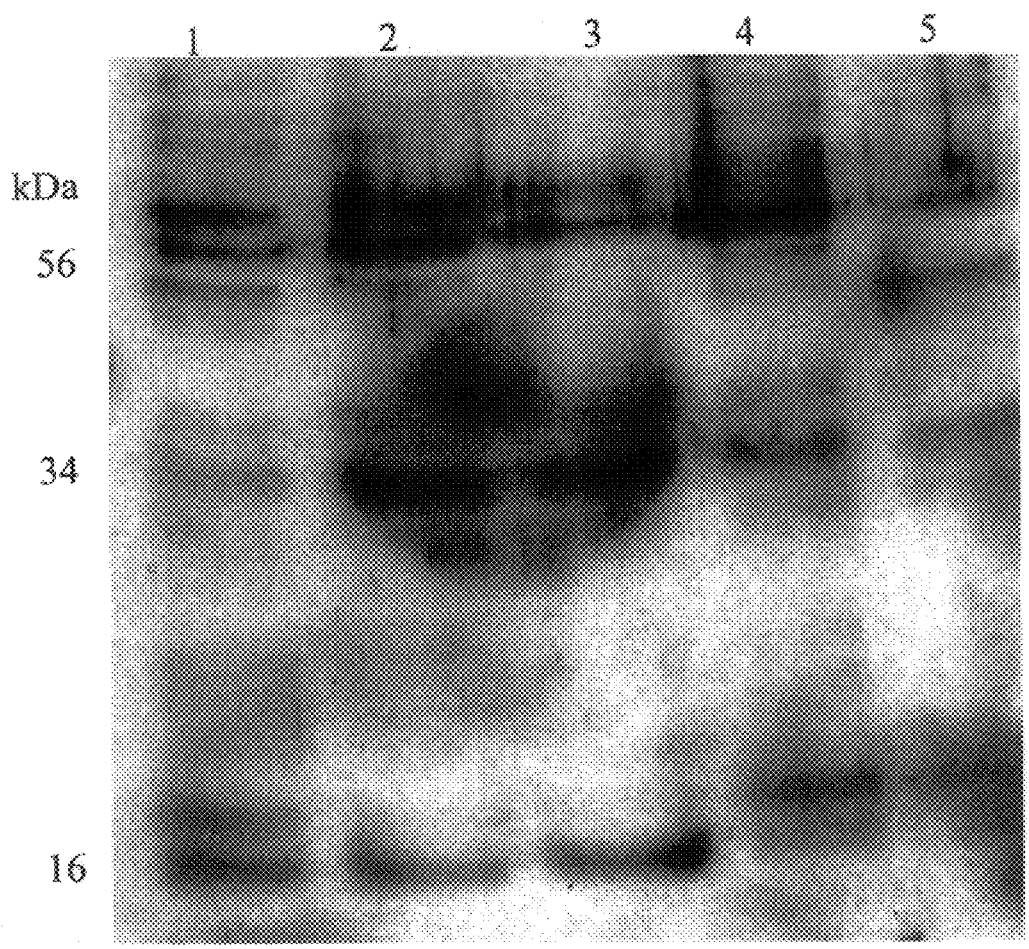
Figure 20A:
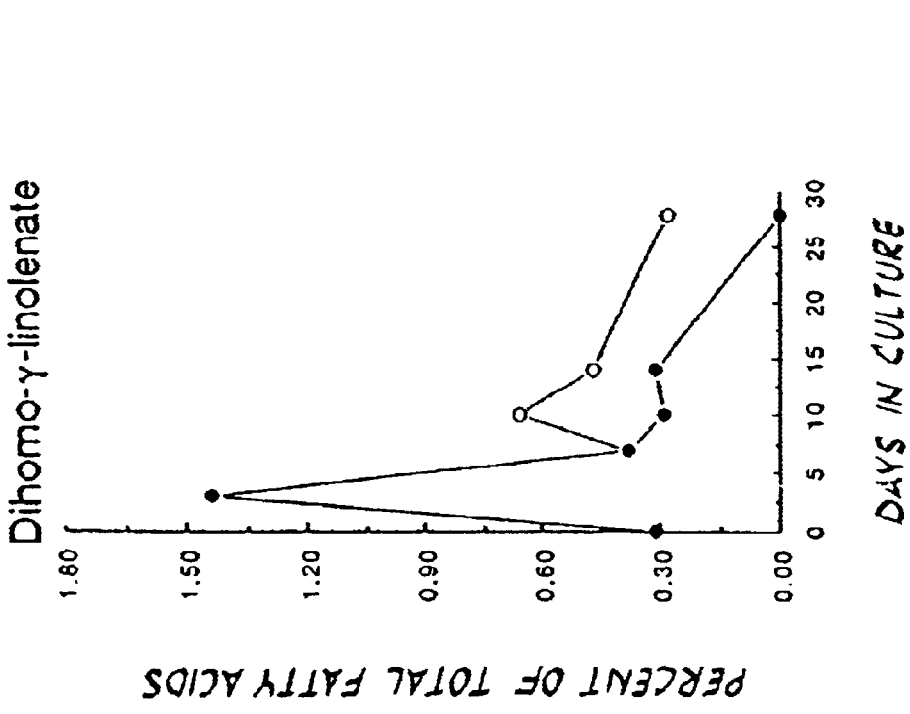
Figure 20B:
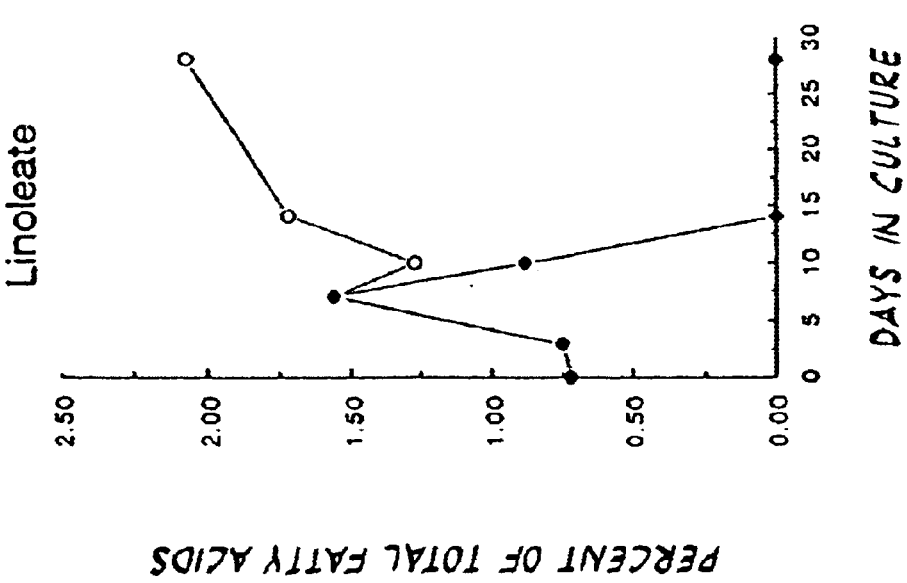
Figure 20C:
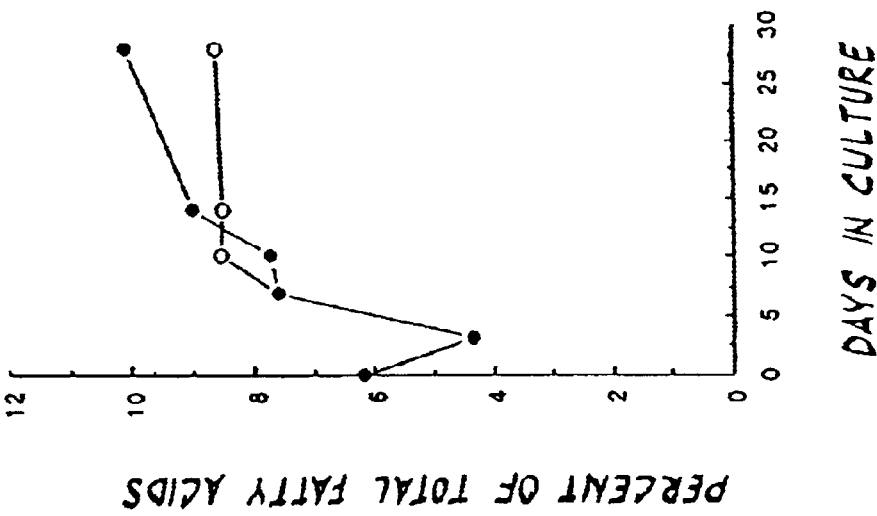
Figure 20D:
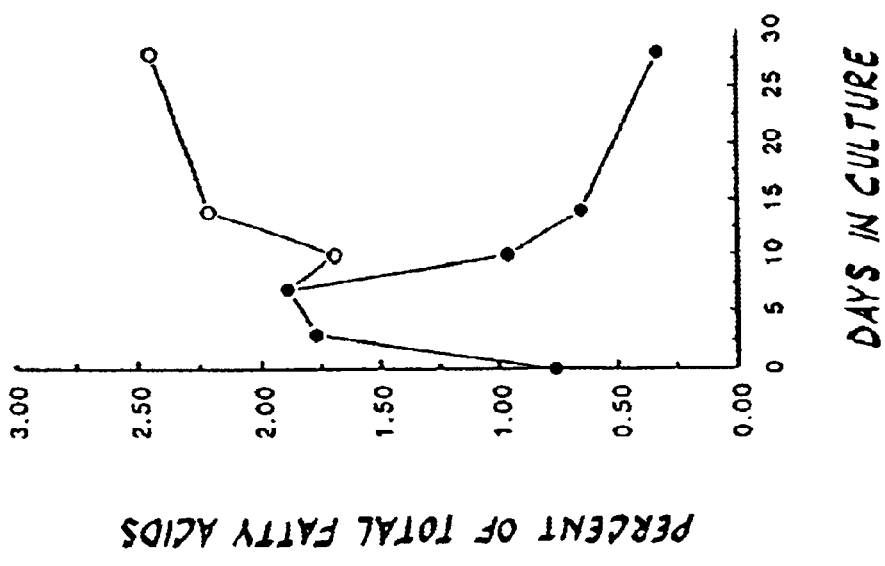

FIG. 19 shows cartilage-derived morphogenetic proteins (CDMP's) in human neocartilage matrix. Neocartilage formed by 90-day cultures of chondrocytes from donors of various ages were extracted in a 1.2 M guanidine-HCl buffer and passed over a heparin affinity column. Proteins were eluted with 1 M NaCl and concentrated using a Centricon filter with a 10K cutoff. The proteins were electrophoresed on a 12% SDS gel under reducing conditions, and transferred to Immobilon (Millipore) membranes. Immunoblots were probed with anti-CDMP antibody (N442) provided by the NIH. The secondary antibody was detected using chemiluminescence. Lanes: 1 (fetal; 2 (1-day neonate); 3 (8-month infant); 4 (12-yr adolescent); 5 (48-year adult). Immunoreactivity was detected in 56 Kd pre-forms, 34 Kd dimers and 14–17 Kd mature proteins.

FIG. 20, in six parts, FIGS. 20A–20F, shows the fatty acid composition of human neocartilage phospho-lipids versus time. Chondrocytes were grown in either the presence (open circles) or absence (filled circles) of 10% serum as described herein and the fatty acid composition of the membrane phospholipids isolated via silicic acid chromatography determined via capillary gas chromatography. The upper panels (FIGS. 20FA, 20FB and 20FC), correspond to the n-6 polyunsaturated fatty acid precursors of eicosanoid synthesis, while the lower panels (FIGS. 20FD, 20FE and 20FF) designate the n-9 fatty acids which are abundant in rapidly growing hyaline cartilage. Notice that Mead acid (20:3 n-9 eicosatrienoic acid) accumulates under serum-free conditions to a level that was two-fold greater than that identified in the native tissue at time zero. Additionally, serum supplementation caused a three-fold accumulation in arachidonate (20:4 n-6). The Mead-to-arachidonate ratio of serum vs. serum-free cultures mirrored that identified in adult and fetal tissue, respectively (Adkisson et al., 1991, supra). Samples were run in duplicate.

Figure 21A:
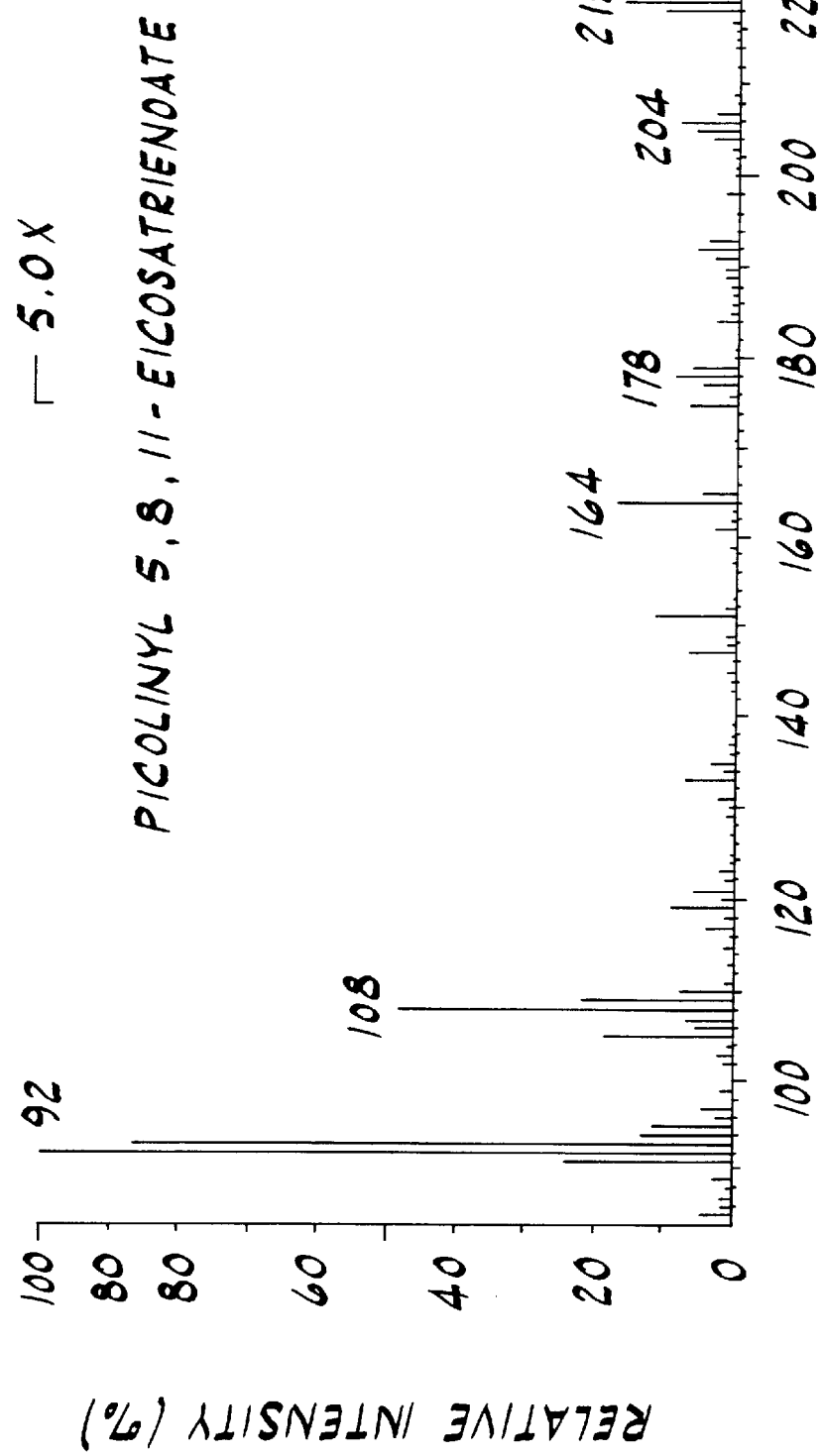
Figure 21B:
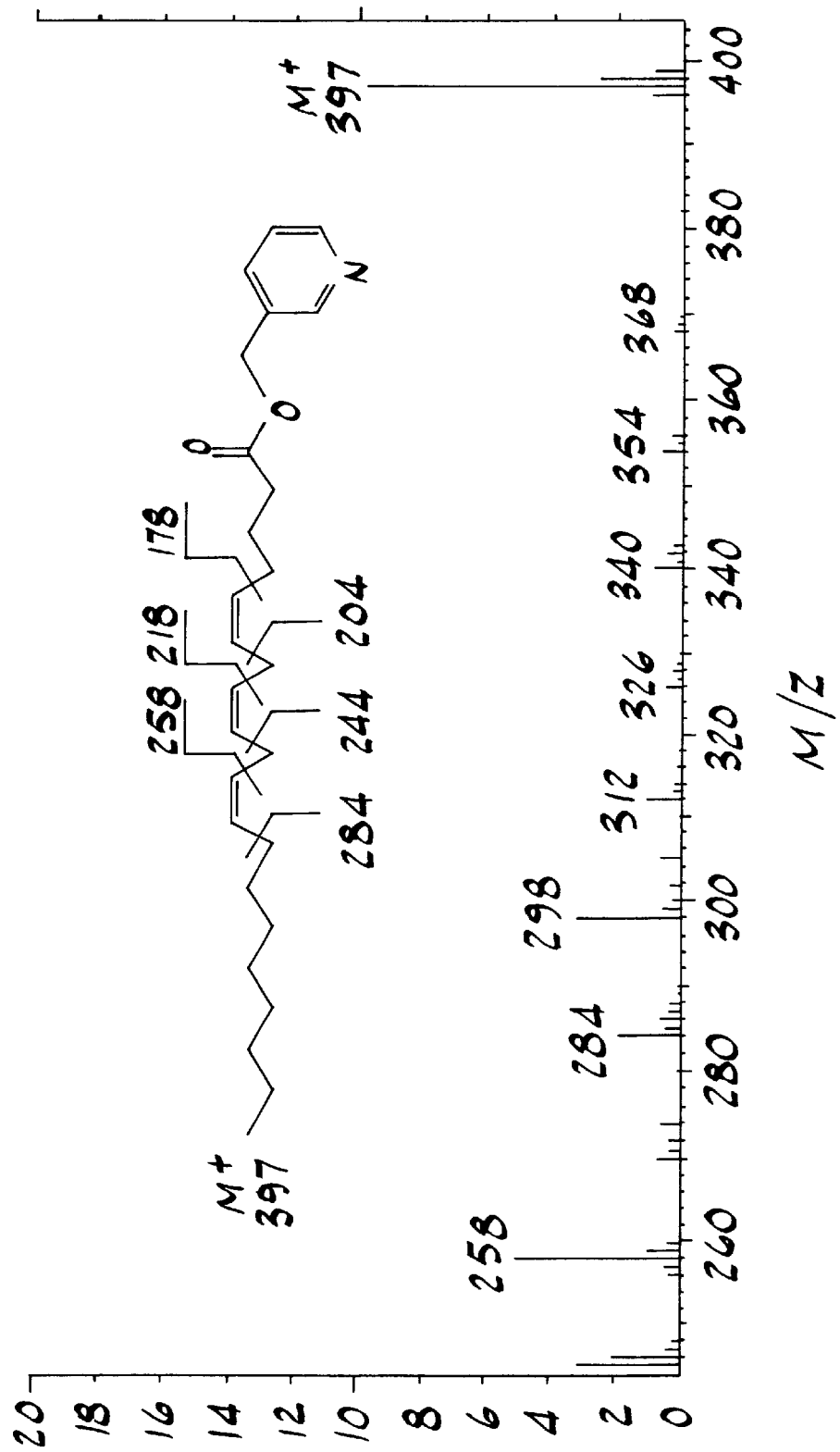

FIG. 21 is a mass chormatogram showing the dominant polyunsaturated fatty acid identified in neocartilage phospholipids (i.e. 20:3 n-9 eicosatrienoic acid) at day 28 of culture. The fragmentation pattern matches that of authentic 20:3 n-9 eicosatrienoic or Mead Acid.

Figure 22A:
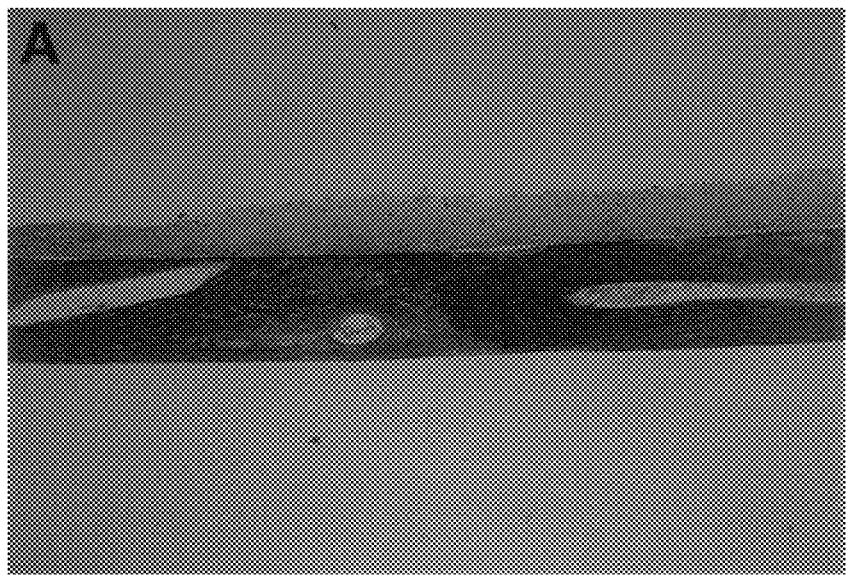
Figure 22B:
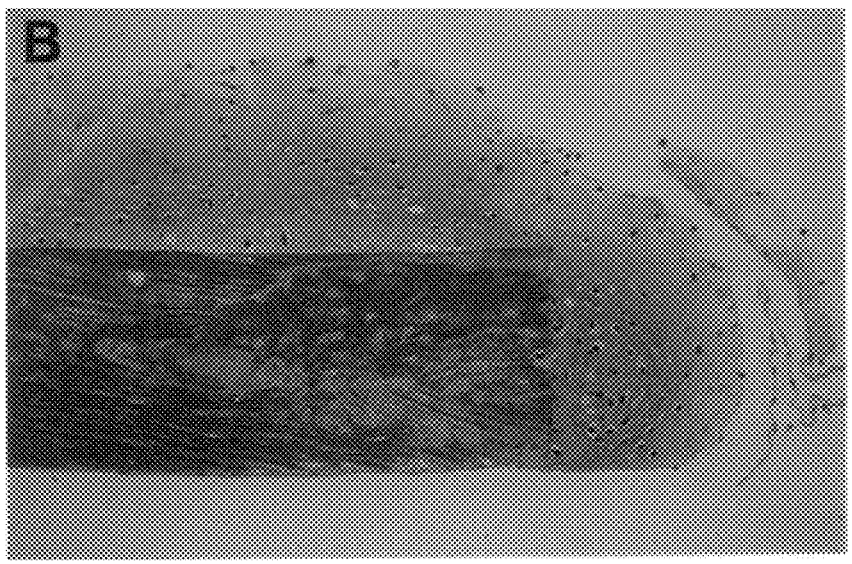

FIG. 22, in two parts, FIGS. 22A and 22B, shows the morphologic appearance of neocartilage/demineralized bone (Lambone) composites following pentachrome staining. Magnification: 22A, 100×; 22B, 200×.

DETAILED DESCRIPTION OF THE INVENTION

In accordance with the present invention, applicant has produced neocartilage tissue which has a morphological appearance largely indistinguishable from healthy native articular cartilage. The cartilage produced is strong, yet malleable. It is readily removable from culture vessels and can be grown with or without the aid of a three-dimensional scaffold. Moreover, this novel cartilage has a membrane phospholipid fatty acid profile which is conducive to resistance to transplant rejection and inflammation. This newly developed biological material also serves as a ready resource for obtaining purified compositions important for applications in biotechnology, including cartilage-specific macromolecules such as high molecular weight aggrecan and collagen types II, VI, IX and XI.

The biological material hereby provided comprises neocartilage having multiple layers of cells surrounded by a substantially continuous insoluble glycosaminoglycan and collagen enriched hyaline extracellular matrix. Furthermore, the membrane phospholipids of the neocartilage are unexpectedly and advantageously enriched in 20:3 n-9 eicosatriene (Mead) fatty acids and depleted in linoleic and arachidonic fatty acids. The Mead acid content is preferably at least about 2% and most preferably, between about 2.5% and 10% of the total fatty acid content. The linoleic acid and arachidonic acid content is preferably, less than about 0.5% and most preferably at least about 0.2% of the total fatty acid content of the membrane phospholipids. This neocartilage is further characterized by its high S-GAG and hydroxyproline content, enrichment in high molecular weight aggrecan, and the relative absence of endothelial, bone and synovial cells, as well as being substantially free of biglycan. Preferably, the neocartilage has a S-GAG content of at least about 400 mg/mg of OH-proline, and more preferably, from aobut 500 mg to about 2500 mg/mg of OH-proline. Preferably, the high molecular weight aggrecan contains at least about 80%, and more preferably, it contains about 90%, of the total cartilage proteglycan content. The chondrocytes of the neocartilage of the present invention are substantially spherical throughout the composition and maintain their articular cartilage phenotype. The neocartilage composition of the present invention is a substantially continuous layer of tissue at least two cell layers thick. After 14 days of growth, the neocartilage had grown to between 10 and 15 cell layers thick. The neocartilage can be grown for at least 120 days to a thickness of at least 2 mm and to a weight of between 300 and 400 mg when 3.8 cm$^2$ dishes are used (15–20 cell layers thick).

The neocartilage can be grown to substantially greater thicknesses when grown under conditions that mimic the biomechanical forces to which articular cartilage is naturally subjected in vivo such as in a compression chamber. It has been found that after 30 days of growth, and as described herein, the glycosaminoglycan content of the neocartilage is approximately 600–1,500 mg S-GAG/mg OH-proline. This is 10 times greater than that of chondrocytes grown in the presence of 10% serum.

The neocartilage may comprise avian or mammalian chondrocytes, preferably human chondrocytes. Additionally, mammalian chondrocytes may be derived from transgenic animals which have been genetically engineered to prevent immune-mediated xenograft rejection (Sandrin, M S et al., *Nature Med* 1:1261–1267, 1995; Sandrin, M S et al., *Xenotransplantation* 3:134–140, 1996; and Osman, N et al., *Proc Nat Acad Sci* 94:14677–14682, 1997). Thus, the neocartilage may be mammalian neocartilage, including human and porcine, or avian neocartilage.

The use of organs/tissues from animal donors (xenotransplantation) is a potential solution to the chronic shortage of allogeneic organs. Porcine tissues are thought to be most suitable for human use due to similarities in size, anatomy and organ physiology between pigs and humans. Recent insights into the mechanisms underlying vascular rejection, endothelial cell activation, and cellular responses to xenogeneic tissue have led to the development of novel strategies designed to inhibit immune-mediated xenograft rejection (Dorling, A., *Expert Opinion on Therapeutic Patents*, 7:1307–1319, 1997).

The neocartilage of the present invention does not require the inclusion of biosynthetic polymer scaffolds in the composition. However, such scaffolds can also be used, if desired. In one alternative embodiment, neocartilage can be grown on demineralized bone allograft forming a composite which is particularly amenable to surgical implementation.

Because the neocartilage of the present invention can be produced free of non-cartilage material, its use as an implant or as replacement tissue provides enhanced biocompatibility. For example scaffold-less neocartilage readily integrates into the surrounding tissue whereas cartilage constructs containing artificial polymer scaffolds are likely to take longer to integrate because the cells must first break down the artificial scaffolds.

In another aspect of the invention, the neocartilage can be used as a replacement tissue for the repair of damaged or defective articular cartilage.

The replacement tissue can be mammalian or avian replacement tissue, most preferably human replacement tissue. Furthermore, mammalian replacement tissue can be produced using chondrocytes from transgenic animals which have been genetically engineered to prevent immune-mediated xenograft rejection.

The replacement tissue can be implanted using procedures well known in the art, such as using traditional surgical means or by implanting orthoscopically.

Surgical implants comprising neocartilage can be surgically implanted and attached to natural cartilage in vivo by sutures or a combination of sutures and biocompatible biological glues, such as tissue trans-glutaminase (Jurgensen et al., *J. Bone J. Surg.* 79A:185–193.)

The neocartilage replacement tissue can also be attached to natural cartilage in vivo by sutureless attachment such as chemical tissue welding.

The neocartilage can be grown to various size specifications to facilitate implantation.

Another embodiment of the invention provides using the neocartilage as a model for studying articular cartilage disease and articular cartilage response to natural and synthetic compounds in vitro. Natural and synthetic compounds of interest such as enzymes, cytokines, growth factors, anti-invasion factors, dedifferentiation factors and pharmacologic agents are generally known in the art.

In particular, the neocartilage may be used in the testing of pharmacologic agents useful in the treatment of diseases of the joint, for example, osteoarthritis and joint inflammation. Arthritis is marked by an increase in the synthesis and release of a variety of cartilage-derived metalloproteinases and mediators of inflammation. Because these enzymes are directly responsible for tissue destruction in arthritis, the matrix metalloproteinases (MMPs) offer excellent drug targets for the development of novel disease-modifying agents. In this aspect, pharmaceuticals are screened for their capacity to modulate arthritic disease. The neocartilage is co-cultured with a candidate pharmaceutical and observed to determine whether characteristics indicative of arthritic modulation are observed. The amounts and conditions employed are largely dependent on the particular pharmaceutical tested and employ methods well known in the art.

In yet another embodiment of the invention, applicant has discovered a novel method for producing neocartilage compositions in vitro from chondrocytes. The method of this embodiment comprises:

isolating chondrocytes;

adhering the chondocyte cells to a surface in a manner effective to produce a cell culture; this may be accomplished by growing the chondrocytes in a growth medium containing an amount of serum effective to allow adherence of the chondrocytes to an appropriate culture vessel;

replacing the growth media containing an amount of serum with a substantially serum-free growth media to produce a substantially serum-free cell culture; and growing the substantially serum-free cell culture to produce neocartilage and neocartilage-derived factors.

In a preferred method, chondrocytes isolated from immature donors such as fetal, neonatal infant, or pre-adolescent chondrocytes are isolated and grown in a substantially serum-free growth media to produce neocartilage.

The chondrocytes used in this method can be avian or mammalian, preferably human chondrocytes. Further, in contrast to other methods of producing neocartilage known in the art, such as seeding cells on three dimensional scaffold material or on material that prevents cellular spreading, further exogenous material is not required to produce three dimensional neocartilage. Unlike methods known in the art, the method of the present invention provides for seeding chondrocytes in direct contact with an appropriate tissue-culture vessel, most preferably uncoated tissue-culture plastic. Although scaffold material is unnecessary, it can be used.

In a preferred embodiment of the invention, a cell culture is produced by isolating immature chondrocytes, e.g., fetal, neonatal, and pre-adolescent chondrocytes from donor articular cartilage.

Chondrocytes may be isolated by methods known in the art such as by sequential enzyme digestion techniques.

The isolated chondrocytes may then be seeded directly on a tissue culture vessel in a basal media comprising an effective amount of serum such as Dulbecco's modified Eagle's medium (DMEM) to allow adherence of the chondrocytes directly to the culture vessel and to promote mitogenesis.

The effective amount of serum added is between 2 and 15% fetal bovine serum, preferably 10%.

The culture medium may also comprise ascorbate, exogenous autocrine growth factors or conditioned growth media as described below.

The cell culture may be grown under suitable culture conditions known in the art such as growing the cell culture at 37 degrees C. in a humidified atmosphere with the addition of 2–10% $CO_2$, preferably 5%.

The growth media containing serum is replaced with growth medium containing half as much serum, preferably 5% of the total growth medium on between day 1 and day 10, preferably on day 7.

On between day 5 and day 14, preferably day 10, the serum containing growth medium is replaced with substantially serum-free growth media to produce a substantially serum-free cell culture.

The preferred substantially serum-free growth media is HL-1, a serum-free media containing insulin-transferrin-selenium-complex as its only source of protein. HL-1 is a registered trademark of Hycor Biomedical, Inc., and also is available from BioWhittaker, Walkersville, Md. Other suitable serum-free growth media will be readily apparent to those skilled in the art.

The substantially serum-free growth media is preferably partially changed periodically throughout the growth period. Following 10 more days in the substantially serum-free medium, the neocartilage of the invention is between 10 and 15 cell layers thick and can be removed from the cell culture with forceps as a rigid disk of neocartilage.

The neocartilage produced by the substantially serum-free cell culture can be grown for at least 300 days. Even after 120 days in culture, the chondrocytes of the neocartilage do not dedifferentiate and fail to synthesize collagen types I, III, and X. The method of the present invention can produce neocartilage of various sizes by using various sized culture vessels.

In yet another aspect of the invention, a method for producing growth media is provided. The method comprises:

isolating fetal chondrocytes;

producing a cell culture by growing isolated chondrocytes in a growth media containing an amount of serum effective to allow adherence of the chondrocytes to an appropriate culture vessel;

replacing the growth media containing an amount of serum with a substantially serum-free growth media after a beginning time interval to produce substantially serum-free cell culture;

growing the substantially serum-free cell culture to produce conditioned growth media; and extracting or concentrating the conditioned growth media from the substantially serum-free cell culture.

The conditioned growth media produced by the method of the present invention can be extracted by means such as heparin affinity chromatography. It may also be concentrated via dialysis and lyophilization. The conditioned growth media thus produced is reserved for future use. The conditioned growth media obtained by this process comprises compounds effective to enhance neocartilage formation such as autocrine factors, dedifferentintion factors, and anti-invasion factors. At least two of these autocrine factors have been identified by applicant as cartilage-derived morphogenetic protein −1 and −2.

When the conditioned growth media is added to the substantially serum free media to between about 5% and 30%, preferably at least about 20% of the total media, it increases the proliferation of neonatal and infant chondrocytes and subsequent deposition of the substantially continuous insoluble glycosaminoglycan and collagen enriched hyaline extracellular matrix.

In order to illustrate the invention in further detail, the following specific laboratory examples were carried out. Although specific examples are thus illustrated herein, it will be appreciated that the invention is not limited to these specific examples or the details therein.

The sources of various materials used in the specific laboratory examples are as follows:

Materials—Dulbecco's modified Eagle's medium (DMEM) with added L-glutamine, sodium pyruvate, and glucose (4.5 g/liter), fetal bovine serum (FBS) and antibiotic (100×) (penicillin G, sodium (10,000 units) and streptomycin sulfate (25 mg/ml of normal saline) were obtained from Life Technologies, Inc. (Grand Island, N.Y.).

Pronase-E (Type XIV, from Streptomyces griseus), hyaluronidase (type III), N-tris[hydroxymethyl]methyl-2-aminoethanesulfonic acid (TES), and MILLEX-GS syringe sterilization filters were obtained from Sigma Chemical Company (St. Louis, Mo.).

Collagenase (CLS II) was purchased from Worthington Biochemicals (Freehold, N.J.). Tissue-culture dishes (12 and 24 well cluster) and bottle top sterilization filter units (type CA) were obtained from Costar Corporation (Cambridge, Mass.).

Bovine serum albumin (fraction V, fatty acid-free) was from Calbiochem (San Diego, Calif.). HL-1 growth media, was obtained from Hycor Biomedical (distributed currently by BioWhittaker).

EXAMPLE 1

Preparation and Culture of Immature and Adult Human Chondrocytes

Chondrocytes were isolated within 8–24 hours of death from the upper region of the tibial plateau and femoral condyle of intact fetal bones (18–21 weeks gestation, Advanced Bioscience Resources, Inc., Alameda, Calif.). Hyaline cartilage from infant knees ($\leq 8$ months) was removed from the metaphysis of both the proximal tibia and distal femur using rib cutters and transferred to sterile serum-free DMEM, containing antibiotics (2×) and 1% bovine serum albumin, for chondrocyte isolation as described below. Additional samples of more mature cartilage (12–58 years) were processed similarly. All of these cartilage tissues were provided by Mid-America Transplant Association (St. Louis, Mo.). All tissues were transported on wet ice prior to use.

Skin from fetal limbs was removed and stored at −20° C. for preparation of collagen standards (i.e., types I and III) via limited pepsinization. Skeletal muscle and other connective tissue were dissected under aseptic conditions to expose the articulating surface of the tibia and femoral condyle. The cruciate ligaments, menisci, and synovial capsule were removed.

Articular cartilage was separated from its underlying epiphysis (i.e., more vascularized region), transferred to the cold synthetic cartilage lymph (SCL) described by Majeska and Wuthier, *Biochim Biophys Acta*, 391:51–60 (1975), and washed extensively (4×) to remove contaminating synovial fluid. Any remaining connective tissue was removed from the cartilage by incubation with 1×trypsin-EDTA (Sigma Chemical Co.) for 30 minutes at 37° C. The enzyme solution was replenished with fresh serum-free DMEM and residual trypsin removed by four additional washes using a vortex mixer.

At this stage of preparation, the cartilage was glistening white in color and showed no evidence of fibrous tissue contamination. Cartilage was then diced into 1 mm cubes, washed and transferred to 50 ml sterile conical tubes (approximately 2 g tissue/tube) containing 7 ml of pronase-E solution (2 mg/ml Sigma Type XIV from *S. griseus*) in HL-1 for 30 minutes digestion at 37° C. in an environmental incubation shaker set at 200 rpm (New Brunswick Scientific). The enzyme solution was removed and 4 ml of HL-1, containing 1 mg/ml BSA, antibiotics and ascorbate (50 $\mu$g/ml) was added. To this solution, 2 ml of stock collagenase (Worthington CLS-II 1,000 units/ml in HL-1) and 1 ml of hyaluronidase (Sigma Type III, 5 mg/ml in HL-1) was added for overnight digestion at 37° C. with mechanical agitation. The following morning cartilage remnants were diluted with 10 ml of fresh media and gently vortexed (3×1 minutes) to release chondrocytes from the remaining extracellular matrix.

Chondrocytes were then separated from tissue debris by gravity filtration through a sterile Falcon cell strainer unit (70 $\mu$m) and sedimented at 600×g for 10 minutes in a clinical centrifuge. Cell viability was greater than 95%. Next, chondrocytes were diluted in DMEM+10% FBS for plating in either 12 or 24 well plastic culture dishes at a density of 1–2×10$^5$ cells/cm$^2$ in 1 ml of growth media and grown at 37° C. in a 95% air, 5% $CO_2$ atmosphere.

Chondrocytes were initially seeded in FBS to promote adherence and to stimulate cell division. Ascorbate (50 $\mu$g/ml, Sigma Chemical, St. Louis, Mo.) was added fresh at plating and at each feeding, generally every 72–96 hours.

On day 7, neocartilage cultures were weaned of serum (5%) and remained 100% serum-free (i.e., in HL-1) from day 10 onward. HL-1 is a chemically defined serum-free media containing insulin-transferrin-selenium-complex as its only source of protein. However, other serum-free media high in arginine and supplemented with insulin-transferrin-selenium may be substituted for HL-1. Where indicated, conditioned media from fetal culture was added to 20% at all media changes to enhance neocartilage formation from infant chondrocytes.

Figure 1A:
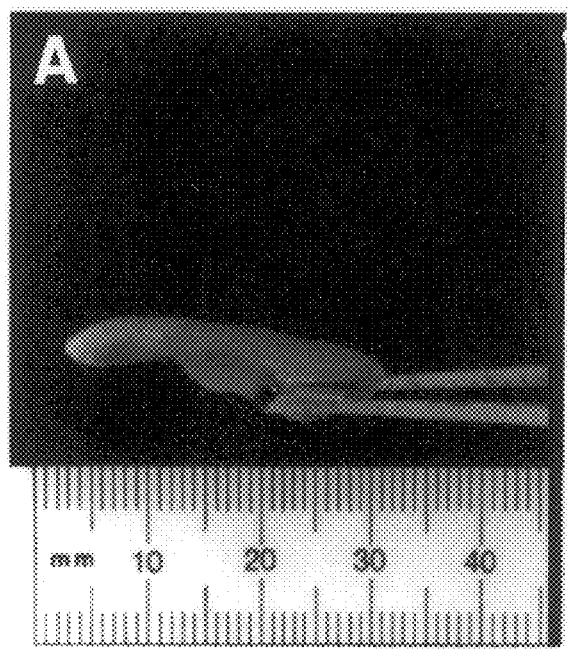
FIGS. 1A and 1B, shows gross morphology of human neocartilage produced in vitro. Fetal chondrocytes grown under serum-free conditions to day 120 produce hyaline tissue that is roughly 1.5–2 mm thick. Wet weights of 300–400 mg were obtained from material grown in 12 well dishes.
Figure 1B:
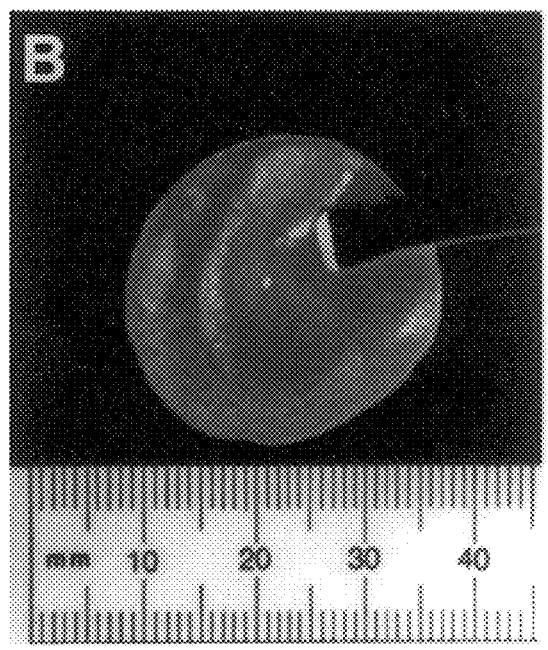

Under the described serum-free conditions, immature chondrocytes displayed tremendous proliferative capacity, as well as the ability to synthesize and deposit an insoluble hyaline cartilage matrix. A gross representation of day 90 neocartilage tissue is shown in FIG. 1. The neocartilage is rigid, yet malleable and was easily removed from culture vessels after day 20 using forceps. This material was strong enough to hold suture material after day 30 of culture and was amenable to surgical implantation at day 40.

Neocartilage cultures were maintained under said conditions and harvested for biochemical and histological analyses between day 1–60 and again at days 90 and 120. Parallel cultures were maintained in DMEM+10% fetal bovine serum for comparison.

EXAMPLE 2

Biochemical Assessment of Neocartilage Formation

Neocartilage formation was assessed by calorimetric analyses of sulfated glycosaminoglycan (S-GAG) and hydroxyproline (OH-proline), general measures of proteoglycan and collagen synthesis, respectively. Neocartilage disks were lyophilized and digested 18 hrs at 56° C. in 500 μl of 0.1 M sodium acetate buffer (pH 5.6), containing 5 mM $Na_4EDTA$, 5 mM L-cysteine, and 125 μg/ml papain. The digests were cooled to room temperature for determination of S-GAG, OH-proline, and DNA content.

Sulfated-GAG and the OH-proline content of papain digested material were determined at the indicated times via microplate calorimetric procedures adapted from Farndale et al., *Biochim Biophys Acta* 883: 173–177 (1986), and Stegemann and Stalder, *Clin Chim Acta* 18: 267–273 (1967), respectively. Chondroitin-6-sulfate (Calbiochem) and cis-4-hydroxy-L-proline (Sigma) were used as standard.

DNA content was estimated by fluorometric analysis using a CytoFluor microplate reader. Bisbenzamide (Hoechst 33258, Sigma Chemical Co., St. Louis, Mo.) was dissolved at 1 mg/ml in water and a working stock diluted further to 0.1 μg/ml in 10 mM tris-HCl, pH 7.4, containing 0.1 M NaCl and 10 mM EDTA.

Ten, 20- and 50-fold dilutions of each sample were prepared and 10 μl aliquots assayed by mixing with 100 μl of dye solution. Fluorescence was read (excitation wavelength=355 nm; emission wavelength=460 nm) and DNA content determined from a standard curve that was constructed using herring sperm DNA (Gibco BRL).

Figure 2:
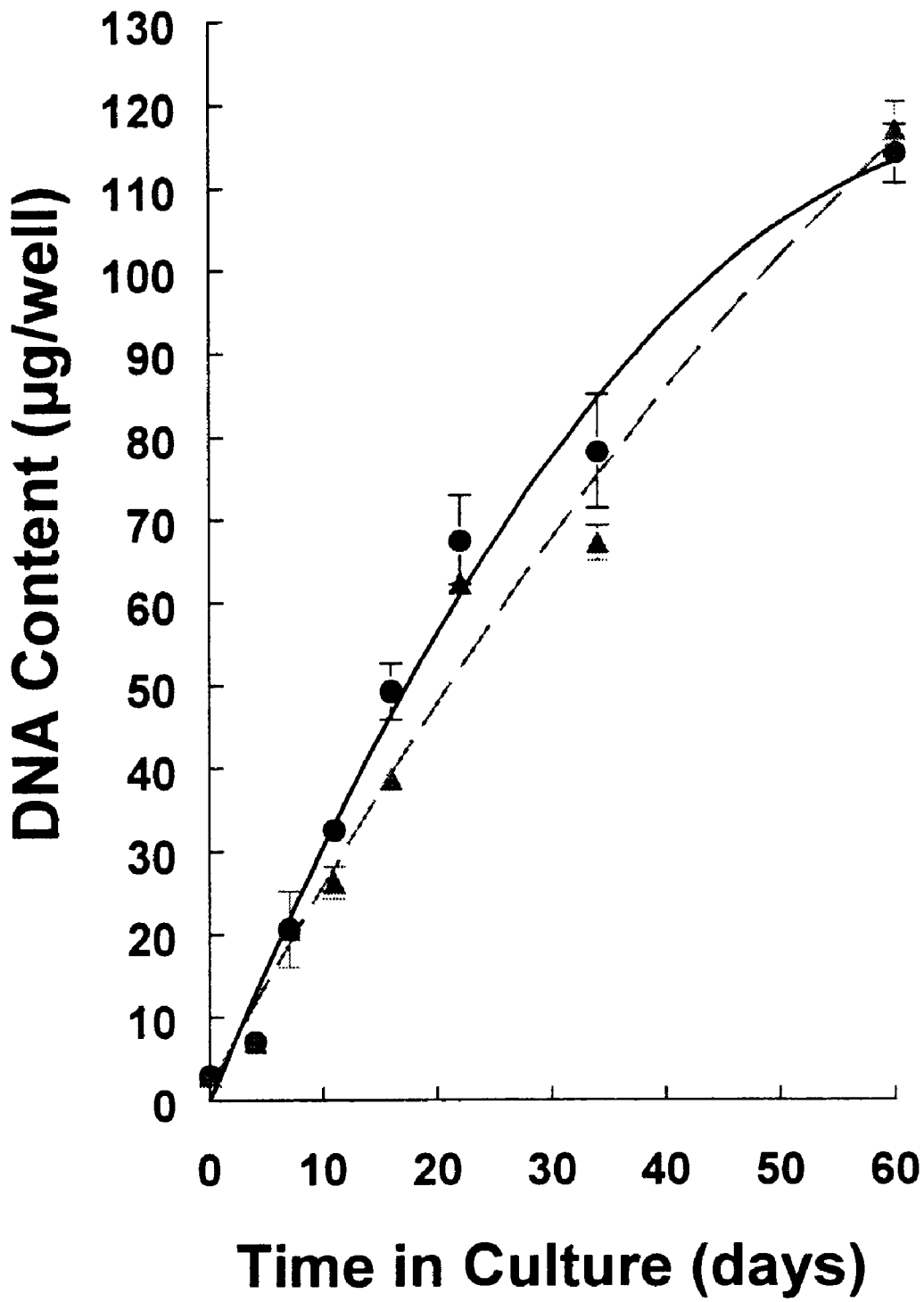
FIG. 2 is a graphical representation which shows growth curves for fetal chondrocytes grown in the presence (solid line) and absence (dashed line) of serum. DNA content was measured over a 60-day time course using Hoechst 33528 fluorescent dye, following papain digestion. Herring sperm DNA was used as standard. Chondrocytes grown under the specified serum-free conditions go through the same number of doublings as those cells grown in the presence of serum.
Figure 3A:
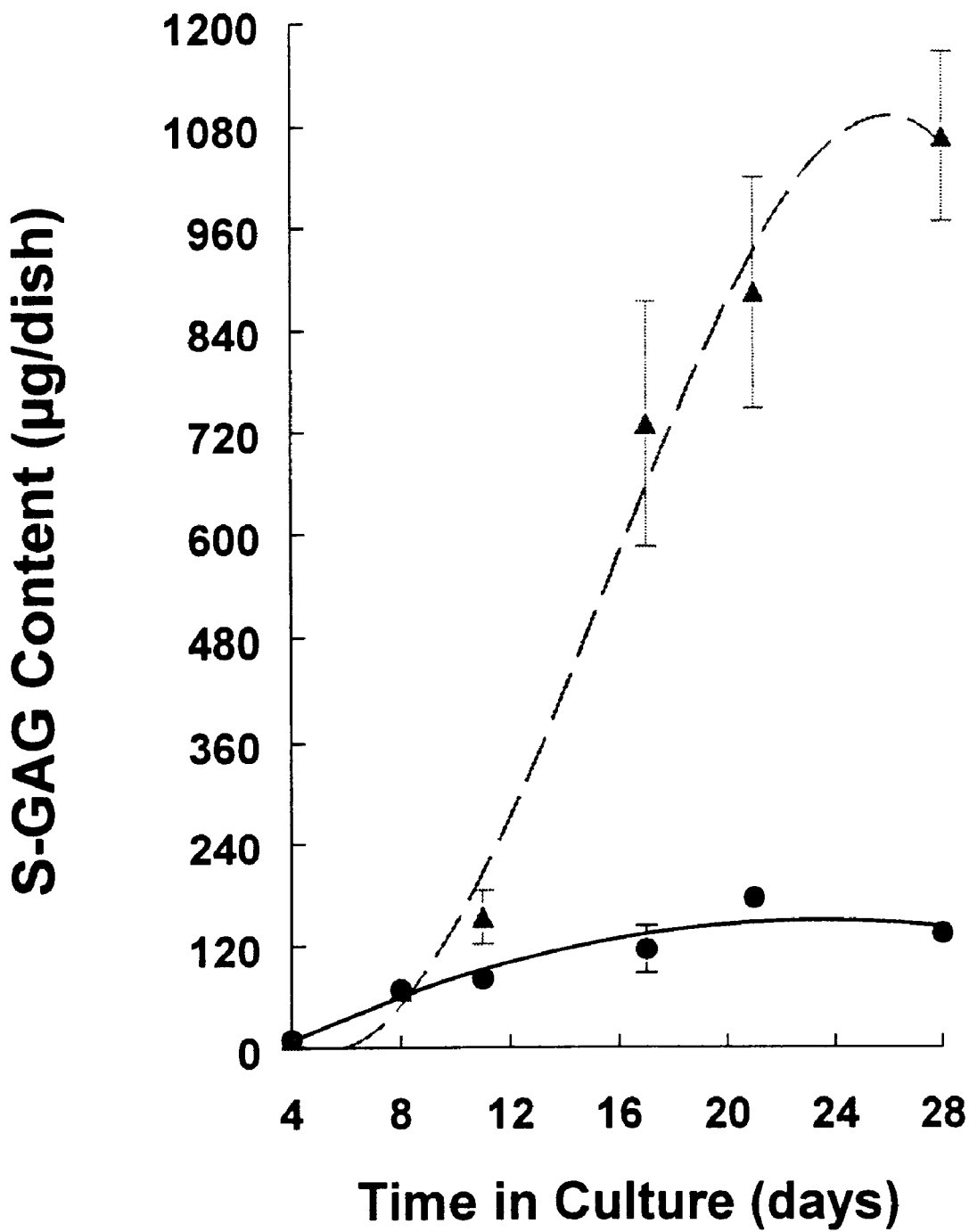
FIGS. 3A and 3B, is a graphical representation which shows that serum deprivation promotes neocartilage formation in vitro: Glycosaminoglycan and collagen deposition by fetal human chondrocytes. Chondrocytes were isolated from the upper region of the proximal tibia and distal femur of human fetal knees (18–21 wks gestation) by sequential enzymatic digestion. Cell suspensions were then filtered, counted, and seeded at high density (24 well clusters) in media containing 10% serum to allow adherence. Upon reaching confluence (day 7), the cultures were subdivided into two groups such that half of the dishes remained serum-free (dashed line), while the remaining dishes were maintained in serum-containing media (solid line). Growth media were supplemented with 50 µg/ml ascorbate at every media change, usually every 72 h. Sulfated glycosaminoglycan (S-GAG) (FIG. 3A), and hydroxyproline (OH-proline) (FIG. 3B), content of the newly synthesized, insoluble hyaline matrix were measured as described hereinbelow. Chondrocytes grown under serum-free conditions produced at least 10-fold greater amounts of proteoglycan (sulfated glycosaminoglycan) and more than 2-fold greater levels of collagen (hydroxyproline) as compared to parallel cultures that were maintained in 10% FBS.
Figure 3B:
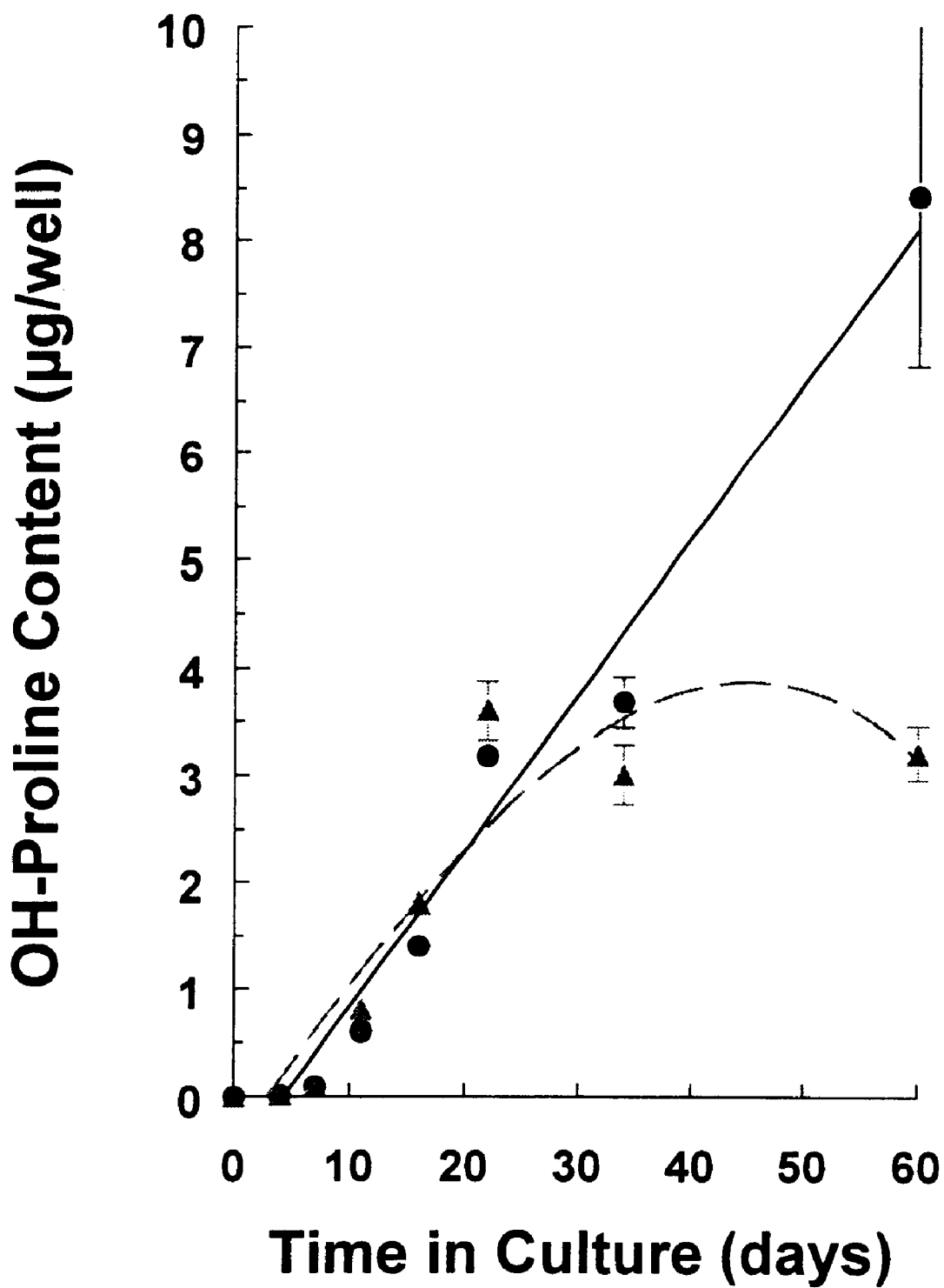
Figure 4A:
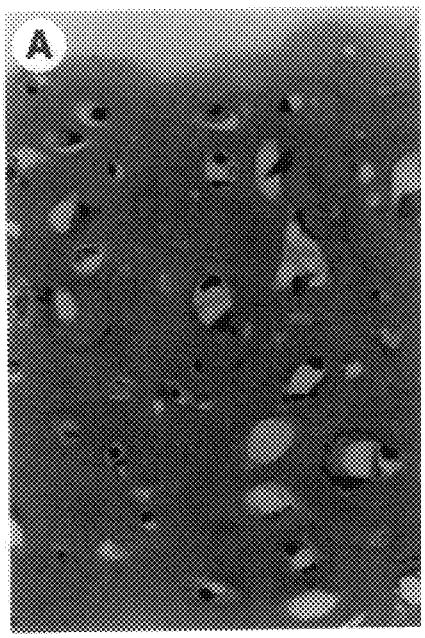
FIGS. 4A and 4B shows the morphologic appearance of human neocartilage (day 56) following serum repletion (10% FBS). Day 28 neocartilage was treated with 10% FBS until termination on day 56 (FIG. 4B), at which point neocartilages were fixed and stained with safranin-O to visualize aggrecan.
Figure 4B:
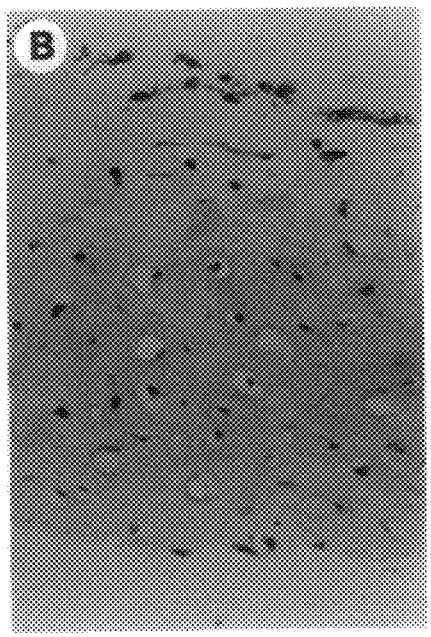

Fetal chondrocytes displayed a rapid proliferative phase of cell growth (FIG. 2) and matrix deposition when grown under serum-free conditions, generating tissue that was 1.5–2.0 mm thick and weighing 300–400 mg (3.8 $cm^2$ dishes) at day 120. In contrast, supplementation with 10% serum reduced total S-GAG and hydroxyproline content by 80–90% at day 30 (FIG. 3). Furthermore, the structural integrity of these samples (+10% serum) was very poor. These samples could not be taken past day 30 of culture without shrinking and balling up. Day 28 neocartilage with 10% serum for an additional 28-day period causes >90% loss in matrix aggrecan (FIG. 4). This effect was titratable, thereby suggesting that either specific components of serum degrade cartilage matrix directly or, alternatively, that serum induces synthesis and/or activation of chondrocyte-derived matrix metalloproteinases.

The potential for neocartilage formation from pre-adolescent and adult articular chondrocytes is depicted in Table I and appears to correlate with skeletal development. Neocartilage formation was not recapitulated in these experiments using articular cartilage obtained from post-adolescent subjects.

TABLE I

Effect of Donor Age on Neocartilage Potential

| Donor Age | Time in Culture (days) | S-GAG (μg) |
|---|---|---|
| Fetal #1 | 30 | 3,583 ± 106 |
| Fetal #2 | 60 | 9,126 ± 30 |
| Fetal #3 | 120 | 7,750 ± 125 |
| Infant (1d) | 25 | 6,853 ± 79 |
| Infant (8 mo) | 300 | 9,664 ± 313 |
| 12 y | 30 | 1,102 ± 117 |
| 20 y | 30 | 107 ± 15 |
| 27 y | 30 | 46 ± 8 |
| 36 y | 30 | 53 ± 13 |
| 43 y | 30 | 31 ± 2 |

High density cultures were established in 12 well clusters as described, and neocartilage formation was allowed to proceed until time of harvest. Triplicate samples were assayed for total S-GAG using dimethyl methylene blue.

Characterization of the morphological appearance and biochemical composition of the tissue revealed an ultrastructural organization that was hyaline in nature and nearly indistinguishable form native articular cartilage. Chondrocytes were constrained to individual lacunae and were encased in an extensive extracellular matrix which stained metachromatically for aggregating proteoglycan (safranin-O) and collagen (pentachrome) (FIG. 5). Moreover, the pentachrome technique failed to identify elastic fibers previously shown to be present in cultures of bovine articular chondrocytes maintained in the presence of serum [Lee et al., *Dev. Biol.* 163: 241–252 (1994)].

Fibrocartilage contamination, a problem typically encountered when articular chondrocytes are cultivated using traditional cell culture methods (i.e., media containing 10% serum), could not be identified in pepsinized extracts of neocartilage material by Western analysis (chemiluminescence detection) or by transmission electron microscopy (TEM) following tissue fixation. The dominant collagen identified by TEM consisted of 20 nm fibrils, while beaded filaments, indicative of type VI collagen, were localized to the lacunae (FIG. 6). Type I collagen fibers typically display a fibril diameter of 100 nm. Western analysis confirmed the presence of type II collagen as the dominant (90%) isotype, and further identified minor cartilage-specific collagens such as collagen types IX and XI (FIG. 7).

Cross reactivity with antibodies to collagen types III and X were also negative in neocartilage, but were reactive in collagen preparations obtained from adult articular cartilage. Thus, the composition of the collagen contained within the neocartilage tissue produced by the method of the invention is indistinguishable in appearance from the starting material from which the cells originated; however, it differs significantly from that of adult and osteoarthritic articular cartilage in that collagen types I, III and X were not detected.

Collagens of the neocartilage matrix can be isolated via pepsinization and neutral salt precipitation (Miller, E J and Rhodes R K; 1982, *Methods of Enzymology* 82:33–64) for use in the production of cartilage biomatrices. The culture conditions described herein are ideal for producing the normal complement and ratio of cartilage collagens, which include but are not limited to types II, VI, IX, and XI.

EXAMPLE 3

Model Systems for Studying Articular Cartilage Disease and Articular Cartilage Response to Natural and Synthetic Compounds Neocartilage cultures were established in 24 or 48 well plastic dishes (Corning) as described above (Example 1) and grown to day 30. The hyaline cartilage matrix was then stimulated to undergo autolytic degradation following 30 day activation with increasing concentrations of a variety of cytokine and/or inflammatory agents, including IL-1, Il-6, IL-17, TNF-α, LPS, and phorbol ester. Culture media were collected every 48 hours and subsequently changed by the addition of fresh media±inflammatory stimuli.

Cultures were terminated and the biochemical composition of the neocartilage matrix that remained was analyzed as described previously. Parallel samples were processed for light and transmission electron microscopy for histological evaluation of extracellular matrix components.

Conditioned media were thawed and identification of chondrocyte-derived metalloproteinases assessed by zymogen substrate gel electrophoresis, as well as Western analysis following SDS-PAGE. Further studies examined the effect of activating agents on synthesis of S-GAG and collagen via radiolabeled incorporation.

Resorption of neocartilage material was readily apparent by gross examination between day 20–25 of stimulation (FIG. 8). Resorption was characterized by a reduction in the diameter of the neocartilage material and its retraction upon removal from the culture vessel, indicating that the structural integrity of the tissue was significantly compromised.

Histological evaluation (i.e., safranin-O and pentachrome staining) of treated and control material revealed a marked reduction in the S-GAG and collagen content of treated samples (FIG. 9). TEM studies also demonstrated a significant alteration in the morphological appearance of the chondrocytes to more of a fibroblast/macrophage lineage (i.e., numerous microvillus projections were identified on the surface of flattened, spindle shaped cells), whereas chondrocytes in untreated controls maintained their rounded phenotype (not shown).

The OH-proline and S-GAG content of treated neocartilage disks were reduced by 20–85% depending on the dose and identity of the activating agent (Table II). Both zymogram and Western analysis identified collagenolytic and casienase activities that were upregulated in the presence of activating agent alone (FIG. 10).

TABLE II

Hydroxyproline content of tissue matrix following chronic cytokine treatment

| Condition | OH-proline content of tissue (pmoles)* |
|---|---|
| Control | 1710 ± 251 |
| +50 mU plasminogen± | 1648 ± 72 |
| IL-1β 0.1 (ng/ml) | 572 ± 105 |
| 1.0 | 541 ± 16 |
| 5.0 | 501 ± 48 |
| +50 mU plasminogen | 460 ± 16 |
| TNFα 1.0 | 403 |
| 5.0 | 355 |

*Samples were lyophilized and digested with papain prior to hydrolysis for determination of OH-proline content via HPLC analysis. ±Human plasminogen was added to enhance the activation of latent MMPs via the plasminogen activator/plasmin cascade.

Phorbol ester specifically induced synthesis of gelatinase B, whereas the cytokine treatments resulted in the production of numerous bands (9–11) on substrate gels, three of which were identified as collagenase 1, 2 and 3 by Western immunoblotting (FIG. 11). Each of these enzymes are implicated in arthritic disease.

This system is unique in that the anabolic and catabolic properties of normal human chondrocyte metabolism can be examined, under defined serum-free conditions. It is clear that the described model of neocartilage formation will facilitate the development and evaluation of pharmacological agents to protect the cartilage matrix from arthritic destruction.

EXAMPLE 4

Surgical Repair of Rabbit Articular Cartilage via Transplantation of Rabbit Neocartilage Allografts Neocartilage allografts were produced from 10-day neonates as described in Example 1. Extreme care was taken to eliminate the use of vascularized epiphyseal cartilage during tissue preparation.

Neocartilage implants were grown to day 30, fixed and stained for histological evaluation, and further extracted for analysis of cartilage specific macromolecules. This procedure yielded hyaline tissue that was enriched in both cartilage specific collagens and glycosaminoglycans (Table III).

TABLE III

Composition of Rabbit Neocartilage

| Component | Relative Abundance |
|---|---|
| Collagen | |
| type I | – |
| type II | +++ |
| type IX | + |
| type XI | + |
| Aggrecan | 14,365 ± 410 μg |

High density cultures were established in 12 well clusters as described, and neocartilage formation was allowed to proceed until harvest on day 40. Triplicate samples were assayed for total S-GAG using dimethyl methylene blue. Isotyping of collagen was performed via electrophoresis on 6.5% SDS-polyacrylamide gels under reduced conditions.

Eighteen (18) skeletally mature (30 wk) male New Zealand White rabbits were divided into three groups to assess the healing potential of transplanted neocartilage at 1, 3, 6 and 12 weeks post-operatively. Rectangular defects of approximately 3 mm in width, spanning the girth of the medial femoral condyle (5 mm), were created surgically in both knees (FIG. 12). Violation of subchondral bone was avoided during this procedure.

Sterile neocartilage implants (day 35–45 in vitro) were subsequently cut to size and sutured into the experimental defect (right side) using 7-0 vicryl suture, anchoring neocartilage to the medial and lateral perichondria, following addition of tissue transglutaminase as described in Jurgensen et al., *J. Bone Joint Surg.* 79-A, 185–193 (1997). Unfilled defects (left side) were allowed to heal intrinsically and served as the contralateral sham control. Arthrotomies were repaired using 4-0 vicryl suture and animals were permitted free cage activity. Oral analgesic was provided for 24 hours post-operatively as needed for pain.

The animals showed excellent tolerance of the surgical procedures, displaying normal ambulation and increased appetite within 24 hours post-operatively. Gross examination of the experimental defects harvested at six weeks revealed good adherence of grafts to surrounding tissue, whereas unfilled defects remained unfilled (FIG. 13).

EXAMPLE 5

Immunological Assessment of Allograft Relection

A one-way mixed leukocyte reaction (MLR) was set up in which chondrocytes, acting as the stimulator population, were first gamma-irradiated in order to block their proliferative potential. Allogeneic leukocytes, obtained from either peripheral blood or buffy coats (American Red Cross) were then passed over a Ficoll gradient. This population of mononuclear leukocytes was counted and subsequently co-cultured with chondrocytes, having first been isolated from day 30–45 neocartilage allografts. Adult cells were also isolated from day 30 cultures which were grown under conditions identical to the neocartilage.

Proliferation of non-irradiated leukocytes was determined on day 7, following a 24 hr pulse with tritiated thymidine (Amersham, 1 µCi/ml) (Abbas, Ark., et al. 1991 *In Cellular and Molecular Immunology*, pp. 320–322). Culture plates were frozen, the cells lysed in water, and the nuclear DNA aspirated and bound to glass filtermats using an automated cell harvester. Filtermats were then dried and counted in a Wallac MicroBeta scintillation counter. Chondrocytes isolated from day 30–45 neocartilage failed to generate an MLR response that would indicate a cross match (FIG. 14B), while the positive controls showed a 19-fold increase in proliferation.

These data support the concept that chondrocytes are immunologically privileged. Although chondrocytes are reported to present MHC class II antigens on their cell surface [Elves, *J. Bone Joint Surg.*, 56B:178–185 (1974); Jahn et al., *Arth Rheum* 30:64–74 (1987); and Jobanputra et al., *Clin. Exp. Immunol.* 90:336–344 (1992)], proliferation of the responder leukocyte population was not detected in three separate assays involving at least twelve (12) different neocartilage samples. From an immunological perspective, these experiments indicate that the present approach to cartilage repair (e.g., allograft transplantation) is feasible.

Additional studies examining the co-stimulatory function of chondrocytes in a T-cell based assay (Abbas, A K, et al. 1991, *In Cellular and Molecular Immnunology*, pp. 320–322) were also negative, indicating that co-stimulatory molecules, probably B7.1 (CD80) and B7.2 (CD86) are not normally expressed by chondrocytes (FIG. 15). Thus, applicant has discovered appropriate culture conditions which permit transplantation of neocartilage into allogeneic recipients.

EXAMPLE 6

Overlaying of Chondrocytes to Increase the Thickness and Structural Integrity of Neocartilage Rabbit and human chondrocytes were isolated, seeded into 12-well dishes and grown to day 10 as described above. During the initial plating of these cultures, $1.4 \times 10^7$ cells were reserved for plating in 100 mm dishes. Cells were subsequently released from the culture surface on day 10 using the collagenase/hyaluronidase procedure described in Example 1.

Chondrocytes were filtered, counted and resuspended in a 1:1 mixture of DMEM+10% FBS/Hl-1, containing ascorbate, at a density of $0.5 \times 10^6$/ml. Day 10 cultures (12-well plates) were overlayed with 1 ml of the cell suspension to increase the thickness and structural integrity of the neocartilage grafts. The cultures were maintained in the 1:1 mix of DMEM/HL-1 from day 13–17, after which they were grown in HL-1 media until harvest at day 40. Total S-GAG in the neocartilage matrix were quantified as described above. FIG. 16 shows that the overlaying procedure increased total S-GAG content by approximately 50%, and as a result increased the rigidity of the neocartilage matrix.

EXAMPLE 7

Isolation and Characterization of Neocartilage Proteoglycan

Neocartilage cultures were established and grown to day 35 as described in Example 1. Newly synthesized proteoglycans were metabolically labeled for 72 hrs using carrier-free [$^{35}$S]-sodium sulfate (55 µCi/ml, Amersham, supra). Following three washes with PBS to remove unincorporated label, the proteoglycans of the neocartilage matrix were extracted in 4M guanidine and precipitated in ethanol. Unlabeled native proteoglycans were also extracted from the articular cartilage of a 12-yr female and 43-yr male for comparison. Twenty (20) µg of S-GAG were loaded and separated on 1.2% agarose gels according to the method of Bjornsson, *Anal. Biochem.*, 210: 292–298 (1993), (FIG. 17).

Greater than 95% of the labeled material was identified as aggrecan, as judged by molecular weight. However, it was noted that this material was of higher molecular weight than the aggrecan found in pre-teen and adult tissue, indicating that the aggrecan monomers were more highly glycosylated. A minor band with electrophoretic mobility identical to that of native decorin was also observed in the neocartilage matrix. Biglycan, present as a minor component of native articular cartilage, was not identified via radiolabel incorporation in 6 replicates of neocartilage. Only 12–15% of the total radiolabeled S-GAG could be recovered in culture supernatant, generating the same profile as that shown here.

Thus, the composition of neocartilage proteoglycan differs from that of mature articular cartilage in two distinct ways. First, biglycan was not identified as a component of the neocartilage matrix; and second, the innate composition of neocartilage proteoglycan appears to be more highly glycosylated, resulting in a high molecular weight aggrecan. It is believed that this aggrecan may play a role in tissue growth and repair by binding specific growth factors with greater avidity than adult aggrecan.

Purification of this material for testing as a wound healing agent is relatively easy and inexpensive. High molecular weight aggrecan bands identified on 1.2% agarose gels were removed and eluted to purity using a BioRad electroelution device. Preliminary studies demonstrate that a 200 mg neocartilage disk yielded 3–4 mg of high molecular weight aggrecan.

EXAMPLE 8

Role of Heparin Binding Proteins in Neocartilage Formation: Identification of Two New Members of the TGF-β Superfamily Fetal chondrocytes were grown as described above and subdivided into three groups on day 10 to investigate the effect of heparin on neocartilage formation. In low doses, heparin is known to increase the activity of certain growth factors, for example the fibroblast growth factor (FGF) family of related proteins, by acting as a co-factor, whereas greater amounts of heparin will strip away certain growth factors from the extracellular matrix and thereby impede tissue repair.

Sterile heparin was added to the media at a final concentration of 0.2, 2.0, and 20 µg for the duration of the culture period (i.e. from day 10–28). Media were exchanged every 3–4 days and recovered for electrophoretic analysis of secreted proteins. Cell layers were removed and the S-GAG (FIG. 18A), hydroxy proline (FIG. 18B), and DNA content quantitated as before (FIG. 18). The highest concentration of heparin caused a severe defect (60% inhibition in S-GAG and 33% in OH-proline) in matrix deposition. This effect was also evident in the 2 µg/ml treatment group, but was much less severe.

When these heparin binding proteins are then extracted from the neocartilage matrix using procedures adapted from Chang et al., approximately 10 proteins showing a molecular mass of less than 60 kDa are visible on a 4–20% gradient Tris/Tricine polyacrylamide gel (FIG. 19). Western blotting using antibodies from the NIH have shown that cartilage derived morphogenetic protein-1 and -2 (CDMP-1 and -2) are present, as was connective tissue derived growth Factor (CTGF) (not shown).

EXAMPLE 9

Serum-free Culture Depletes Neocartilage of Precursor Fatty Acids for Eicosanoid Synthesis Adkisson et al., *FASEB J* 5: 344–353 (1991), discovered high concentrations of 20:3 n-9 eicosatrienoic acid and low concentrations of n-6 polyunsaturated fatty acids (PUFA) in normal, rapidly growing cartilages of several vertebrates, a biochemical hallmark of essential fatty acid deficiency. Because the n-6 fatty acids, in particular arachidonic acid (20:4 n-6), are key mediators of inflammation and transplant rejection (Schreiner et al., *Science* 240: 1032–1033 (1988), the fatty acid composition of neocartilage grafts were characterized during a 28-day time course in vitro.

Total cellular lipids and the phospholipid fraction were isolated as described in Adkisson et al., supra. Pentafluorobenzyl ester derivatives of the free fatty acids obtained from the phospholipid fraction were prepared for microanalysis by capillary gas chromatography using a SP-2380 fused silica column (Supelco Inc., Bellefonte, Pa.). The gas chromatograph (HP model 5890) was held at 160° C. for 2 min., temperature programmed at 10° C./min to 200° C., and maintained at this temperature for an additional 10 min. Both the injector and the electrochemical detector temperatures were set at 225° C. Derivatized fatty acids were identified by co-migration with authentic standards, while unusual fatty acids were characterized by their fragmentation pattern using mass spectrometry analysis of their picolinyl ester derivative as described previously (Adkisson et al., 1991). Percent composition of individual fatty acids was determined by integration using Hewlett-Packard model 3393A integrator.

FIG. 20 illustrates that essential fatty acids, a component of the culture media (i.e., 5–10% FBS from day 1–10), are rapidly incorporated into the phospholipid stores of isolated chondrocytes. Moreover, it is clear that once the cultures are switched to and maintained in serum-free HL-1 media (closed circles), the native complement of fatty acids is restored, such that low levels of the n-6 PUFAs are detected. The n-6 fatty acids, shown in the upper three panels, continue to accumulate in chondrocyte phospholipids when the neocartilage cultures are maintained in serum-containing media (open circles).

FIG. 21 is a mass chromatogram of the dominant polyunsaturated fatty acid identified in neocartilage phospholipids (i.e. 20:3 n-9 eicosatrienoic acid) at day 28 of culture. The fragmentation pattern matches that of authentic 20:3 n-9 eicosatrienoic or Mead Acid.

It is unclear whether enrichment in n-9 fatty acids reduces antigen expression of MHC class II molecules or B7 co-stimulatory molecules which are required to establish immunogeneity in allograft rejection. The literature does support the fact that a dearth of n-6 PUFA modulates the infiltration of inflammatory cells by inhibiting leukotriene formation (Cleland et al., 1984, *Lipids* 29:151–155, and Schreiner et al., 1988, supra). This in turn protects organs from possible transplant rejection.

In summary, the novel serum-free culture system used to produce neocartilage tissue may facilitate allogeneic transplantation of the neocartilage by regulating chondrocyte immunogenicity, as well as the elaboration of inflammatory eicosanoids/cytokines.

EXAMPLE 10

Preparation of Neocartilage/Demineralized Bone Composites

Day 60 neocartilage cultures were enzymatically dispersed as described in Example 1 one million chondrocytes were then seeded onto samples of demineralized allograft bone (Lambone™, 100–300 µm thick) which were first trimmed to accomodate in vitro culture in 12 well clusters. Lambone™, obtained from Pacific Coast Tissue Bank, Los Angeles, Calif., was washed extensively in culture media to remove residual ethylene oxide gas used during tissue processing.

Neocartilage formation on demineralized allograft bone was allowed to proceed to day 28 as described herein. Neocartilage/Lambone composites were then rinsed and fixed overnight in 10% neutral buffered formalin for morphological examination via pentachrome staining.

FIG. 22A and B illustrate the morphologic appearance of neocartilage/Lambone™ composites following pentachrome staining. Magnification: 22A, 100×; 22B 200×.

In view of the above, it will be seen that the several objects of the invention are achieved.

As various changes could be made in the above compositions and methods by the person skilled in the art after reading the present disclosure without departing from the spirit and scope of the invention, it is intended that all matter contained in the above description shall be interpreted as illustrative of the claimed invention and not in a limiting sense.

What is claimed is:

1. A method for growing neocartilage comprising: isolating chondrocytes; adhering said chondrocytes to a surface using means effective to produce a cell culture; and growing said cell culture in a substantially serum-free growth media to produce neocartilage.

2. A method for growing neocartilage as set forth in claim 1 wherein said adhering means comprise growing said chondrocytes in a growth media containing an amount of serum effective to allow adherence of said chondrocytes.

3. The method of claim 2, wherein the method further comprises adding to said substantially serum-free cell culture an amount of conditioned growth media effective to enhance neocartilage formation.

4. The method of claim 2, wherein the method further comprises adding ascorbate to said cell culture.

5. The method of claim 1, wherein said chondrocytes are immature chondrocytes.

6. The method of claim 1, wherein said chondrocytes are human chondrocytes.

7. The method of claim 3, wherein said conditioned growth media is between approximately 5 percent and 30 percent of said substantially serum-free growth media.

8. The method of claim 3, wherein said conditioned growth media is approximately 20 percent of said substantially serum-free growth media.

9. The method of claim 1, wherein said substantially serum-free growth media comprises growth factors for the proliferation of said chondrocytes.

10. The method of claim 3, wherein said conditioned growth media comprises growth factors for the proliferation of said chondrocytes.

11. The method of claim 10, wherein said growth factors are autocrine factors.

12. The method of claim 3, wherein said conditioned growth media contains factors for the differentiation of said chondrocytes.

13. The method of claim 3, wherein said conditioned growth media contains factors for the anti-invasion of non-chondrocytic cells.

14. A method of claim 1 wherein said substantially serum-free growth media is HL-1.

15. A method of claim 3 wherein said conditioned growth media comprises cartilage-derived morphogenic protein-1.

16. A method of claim 3 wherein said conditioned growth media comprises cartilage-derived morphogenic protein-2.

17. A method of claim 2 wherein said growth media comprises between approximately 2 and 15 percent fetal bovine serum.

18. A method of claim 17 wherein said growth media comprises approximately 10 percent fetal bovine serum.

19. A method of claim 1 wherein the method further comprises growing said cell culture at 37 degrees Celsius in a humidified atmosphere with the addition of approximately 2 to 10 percent $CO_2$.

20. A method of claim 19 wherein said cell culture is grown at 37 degrees Celsius in a humidified atmosphere with the addition of approximately 5 percent $CO_2$.

21. A method of claim 1 wherein said neocartilage is enriched in Mead acid.

22. A method of claim 1 wherein said neocartilage is substantially free of endothelial, bone and synovial cells.

23. A method of claim 1 wherein said neocartilage is substantially free of type I, III and X collagen.

24. A method of claim 1 wherein said neocartilage is enriched in high molecular weight aggrecan.

25. A method of claim 1 wherein said neocartilage is substantially free of biglycan.

26. A method of claim 1 wherein said neocartilage comprises multiple layers of cells surrounded by a continuous insoluble glycosaminoglycan and collagen enriched hyaline extra cellular matrix containing no biglycan.

27. A method of claim 1 wherein said neocartilage comprises multiple layers of cells surrounded by a continuous insoluble glycosaminoglycan and collagen enriched hyaline extra cellular matrix depleted in both linoleic acid and arachidonic acid.

28. A method of claim 1 wherein said neocartilage is characterized as follows:

(a) containing membrane phospholipids enriched in Mead acid and depleted in linoleic and arachidonic acid;

(b) being enriched in high molecular weight aggrecan;

(c) being substantially free of endothelial, bone and synovial cells;

(d) being substantially free of biglycan.

* * * * *